(12) United States Patent
Chappa

(10) Patent No.: US 8,961,457 B2
(45) Date of Patent: Feb. 24, 2015

(54) CATHETER ASSEMBLY WITH GUARD

(75) Inventor: Ralph A. Chappa, Ham Lake, MN (US)

(73) Assignee: Surmodics, Inc., Eden Prairie, MN (US)

( * ) Notice: Subject to any disclaimer, the term of this patent is extended or adjusted under 35 U.S.C. 154(b) by 375 days.

(21) Appl. No.: 13/248,462

(22) Filed: Sep. 29, 2011

(65) Prior Publication Data

US 2012/0083733 A1 Apr. 5, 2012

Related U.S. Application Data

(60) Provisional application No. 61/388,380, filed on Sep. 30, 2010.

(51) Int. Cl.
  *A61M 37/00* (2006.01)
  *A61M 25/10* (2013.01)
  *A61M 25/00* (2006.01)

(52) U.S. Cl.
  CPC ....... A61M 25/10 (2013.01); *A61M 2025/0057* (2013.01); *A61M 2025/105* (2013.01); *A61M 2025/1081* (2013.01)
  USPC .................................................. 604/103.02

(58) Field of Classification Search
  CPC . A61L 2420/02; A61L 2420/08; A61L 27/56; A61M 29/00; A61L 31/00; A61M 2025/105; A61M 25/10; A61M 25/104; A61M 2025/1086; A61M 2025/1081; A61M 2025/1031; A61M 2025/0057; A61M 31/002
  USPC ............. 424/423; 604/103.02–103.09, 96.01; 623/1.11
  See application file for complete search history.

(56) References Cited

U.S. PATENT DOCUMENTS

| | | | |
|---|---|---|---|
| 5,102,402 A * | 4/1992 | Dror et al. ...................... | 604/265 |
| 5,414,075 A | 5/1995 | Swan et al. | |
| 5,876,374 A * | 3/1999 | Alba et al. ............... | 604/164.08 |
| 5,893,840 A * | 4/1999 | Hull et al. ................ | 604/103.02 |
| 6,007,833 A | 12/1999 | Chudzik et al. | |
| 6,278,018 B1 | 8/2001 | Swan | |
| 6,544,579 B1 | 4/2003 | Landon | |
| 6,703,040 B2 | 3/2004 | Katsarava et al. | |
| 6,991,617 B2 * | 1/2006 | Hektner et al. .......... | 604/103.01 |
| RE40,359 E | 6/2008 | Katsarava et al. | |
| 7,491,188 B2 * | 2/2009 | Holman et al. .......... | 604/103.01 |

(Continued)

FOREIGN PATENT DOCUMENTS

WO    WO 2005/068533 A1    7/2005

OTHER PUBLICATIONS

International Search Report and Written Opinion mailed Dec. 19, 2011.

(Continued)

*Primary Examiner* — Nicholas Lucchesi
*Assistant Examiner* — Diva K Chander
(74) *Attorney, Agent, or Firm* — Kagan Binder, PLLC

(57) ABSTRACT

A catheter assembly includes an expandable and collapsible structure having an outer surface. The expandable and collapsible structure is adapted to expand between a contracted state and a dilated state. A guard is bonded to the outer surface of the expandable and collapsible structure. The guard and the expandable and collapsible structure cooperatively define a plurality of reservoirs. A coating disposed in the reservoirs. The coating includes a bioactive agent. The coating protrudes from the reservoirs when the expandable and collapsible structure is expanded to the dilated state.

38 Claims, 8 Drawing Sheets

(56) References Cited

U.S. PATENT DOCUMENTS

| | | | |
|---|---|---|---|
| 8,048,028 B2 * | 11/2011 | Horn et al. | 604/103.08 |
| 8,162,880 B2 * | 4/2012 | Jayaraman | 604/103.02 |
| 2004/0087902 A1 * | 5/2004 | Richter | 604/103.02 |
| 2004/0138733 A1 * | 7/2004 | Weber et al. | 623/1.11 |
| 2006/0030669 A1 | 2/2006 | Taton et al. | |
| 2006/0182873 A1 * | 8/2006 | Klisch et al. | 427/2.1 |
| 2007/0106216 A1 * | 5/2007 | Noddin | 604/103.09 |
| 2007/0218102 A1 | 9/2007 | Chudzik et al. | |
| 2007/0224247 A1 | 9/2007 | Chudzik et al. | |
| 2007/0260054 A1 | 11/2007 | Chudzik | |
| 2008/0140002 A1 * | 6/2008 | Ramzipoor et al. | 604/103.02 |
| 2009/0226502 A1 * | 9/2009 | Chen | 424/423 |
| 2010/0036481 A1 * | 2/2010 | Dubrul et al. | 623/1.42 |
| 2010/0285085 A1 * | 11/2010 | Stankus et al. | 424/423 |
| 2010/0324645 A1 * | 12/2010 | Stankus et al. | 623/1.11 |

OTHER PUBLICATIONS

International Preliminary Report on Patentability, PCT/US2011/054180, mailed Apr. 11, 2013.

* cited by examiner

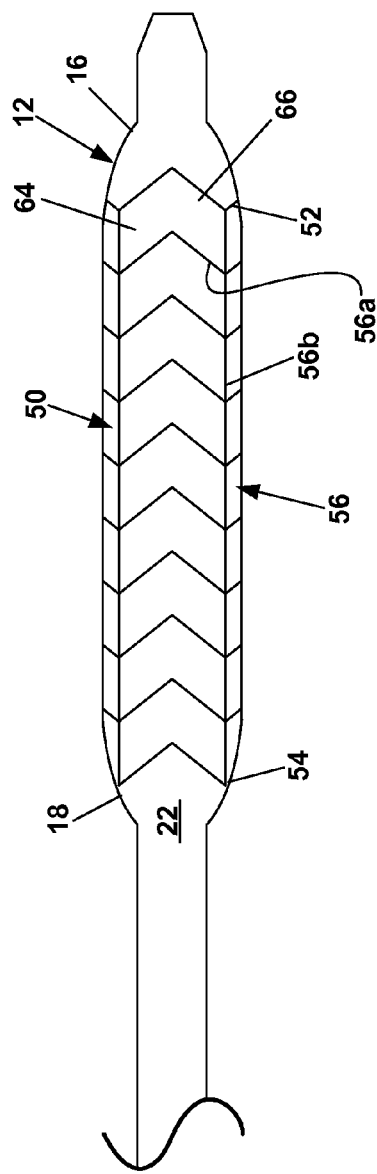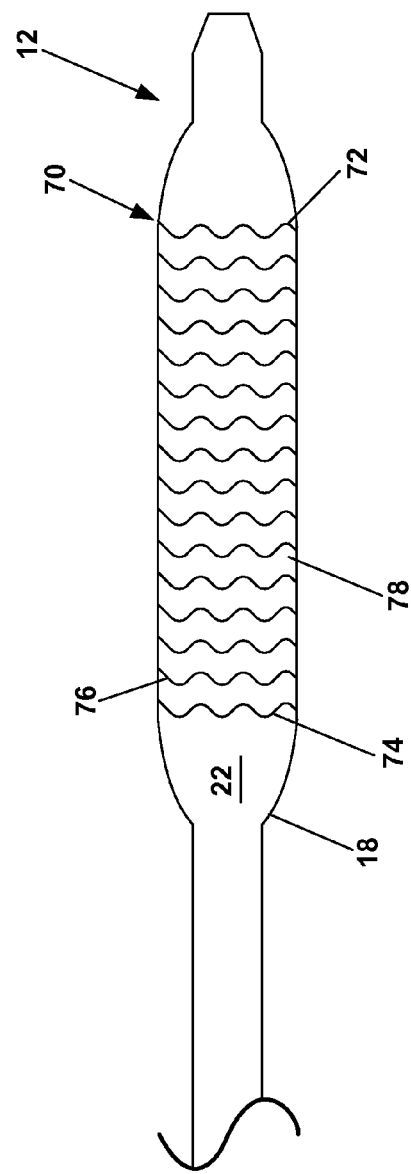
FIG. 5
FIG. 6

CATHETER ASSEMBLY WITH GUARD

CROSS REFERENCE TO RELATED APPLICATIONS

This application claims benefit of U.S. Provisional Application No. 61/388,380, filed Sep. 30, 2010, which application is incorporated herein by reference.

BACKGROUND

The release of drugs from an implanted medical device has been shown to be beneficial for the function of devices and the treatment of various medical conditions. For example, delivery of a drug from the device surface can prevent cellular responses initiated by the presence of the implantable device. Also, drug released from the device can prevent conditions that would otherwise shorten the functional life of the device following implantation. Drug released from the device may also be directed at treating a diseased area of the body.

Some implantable devices simply have a drug applied to the device surface. Such preparations are generally undesirable because the drug can be easily removed from the surface during insertion.

Implantable medical devices having thin polymeric coatings containing therapeutic compounds protect and control the release of drug from the device surface. Such devices have been shown to be particularly valuable for the treatment of diseases of the cardiovascular system. However, these polymeric coatings may not be ideal for applications involving the transient insertion of a medical device to a target tissue in the body.

SUMMARY

An aspect of the present disclosure relates to a catheter assembly. The catheter assembly includes an expandable and collapsible structure having an outer surface. The expandable and collapsible structure is adapted to expand between a contracted state and a dilated state. A guard is bonded to the outer surface of the expandable and collapsible structure. The guard and the expandable and collapsible structure cooperatively define a plurality of reservoirs. A coating disposed in the reservoirs. The coating includes a bioactive agent. The coating protrudes from the reservoirs when the expandable and collapsible structure is expanded to the dilated state.

Another aspect of the present disclosure relates to a catheter assembly. The catheter assembly includes an expandable and collapsible structure having an outer surface. The expandable and collapsible structure is adapted to expand between a contracted state and a dilated state. The expandable and collapsible structure is made of a first material. A guard is bonded to the outer surface of the expandable and collapsible structure. The guard is made of a second material that is less flexible than the first material. The guard and the expandable and collapsible structure cooperatively define a plurality of reservoirs. The outer surface of the expandable and collapsible structure forming base walls of the reservoirs and the guard forming sidewalls of the reservoirs. A coating disposed in the reservoirs. The coating includes a bioactive agent. The coating protrudes from the reservoirs when the expandable and collapsible structure is expanded to the dilated state.

Another aspect of the present disclosure relates to a catheter assembly. The catheter assembly includes an expandable and collapsible structure having an outer surface, the expandable and collapsible structure is adapted to expand between a contracted state and a dilated state. A guard is disposed on the outer surface of the expandable and collapsible structure. The guard includes a fold line that extends between a first end of the guard and an oppositely disposed second end. The fold line has an area of reduced thickness. The guard and the collapsible structure cooperatively define a plurality of reservoirs with the outer surface of the expandable and collapsible structure forming base walls of the reservoirs and the guard forming sidewalls of the reservoirs. A coating is disposed in the reservoir. The coating includes a bioactive agent. The coating protrudes from the reservoirs when the expandable and collapsible structure is expanded to the dilated state.

Another aspect of the present disclosure relates to a method of applying a coating to a catheter assembly. The method includes heating a coating so that the coating is in a flowable state. A measured amount of coating is applied to reservoirs that are cooperatively defined by an expandable and collapsible structure of the catheter assembly and a guard that is bonded to an outer surface of the expandable and collapsible structure. The coating is cooled so that the coating is in a non-flowable state.

Another aspect of the present disclosure relates to a method of applying a coating to a catheter assembly. The method includes applying a coating to an exterior surface of a guard that is affixed to an expandable and collapsible structure of a catheter assembly. The guard and the expandable and collapsible structure defining a plurality of reservoirs having openings at the exterior surface of the guard. The guard and the expandable and collapsible structure are placed in an inner bore of a sheath. The coating is heated so that the coating is in a flowable state. The guard and the expandable and collapsible structure are slid out of the sheath so that the coating on the exterior surface of the guard is substantially removed.

A variety of additional aspects will be set forth in the description that follows. These aspects can relate to individual features and to combinations of features. It is to be understood that both the foregoing general description and the following detailed description are exemplary and explanatory only and are not restrictive of the broad concepts upon which the embodiments disclosed herein are based.

DRAWINGS

FIG. 5 is a side view of an alternate embodiment of the catheter assembly.

FIG. 6 is a side view of an alternate embodiment of the catheter assembly.

DETAILED DESCRIPTION

Reference will now be made in detail to the exemplary aspects of the present disclosure that are illustrated in the accompanying drawings. Wherever possible, the same reference numbers will be used throughout the drawings to refer to the same or like structure.

Figure 1:
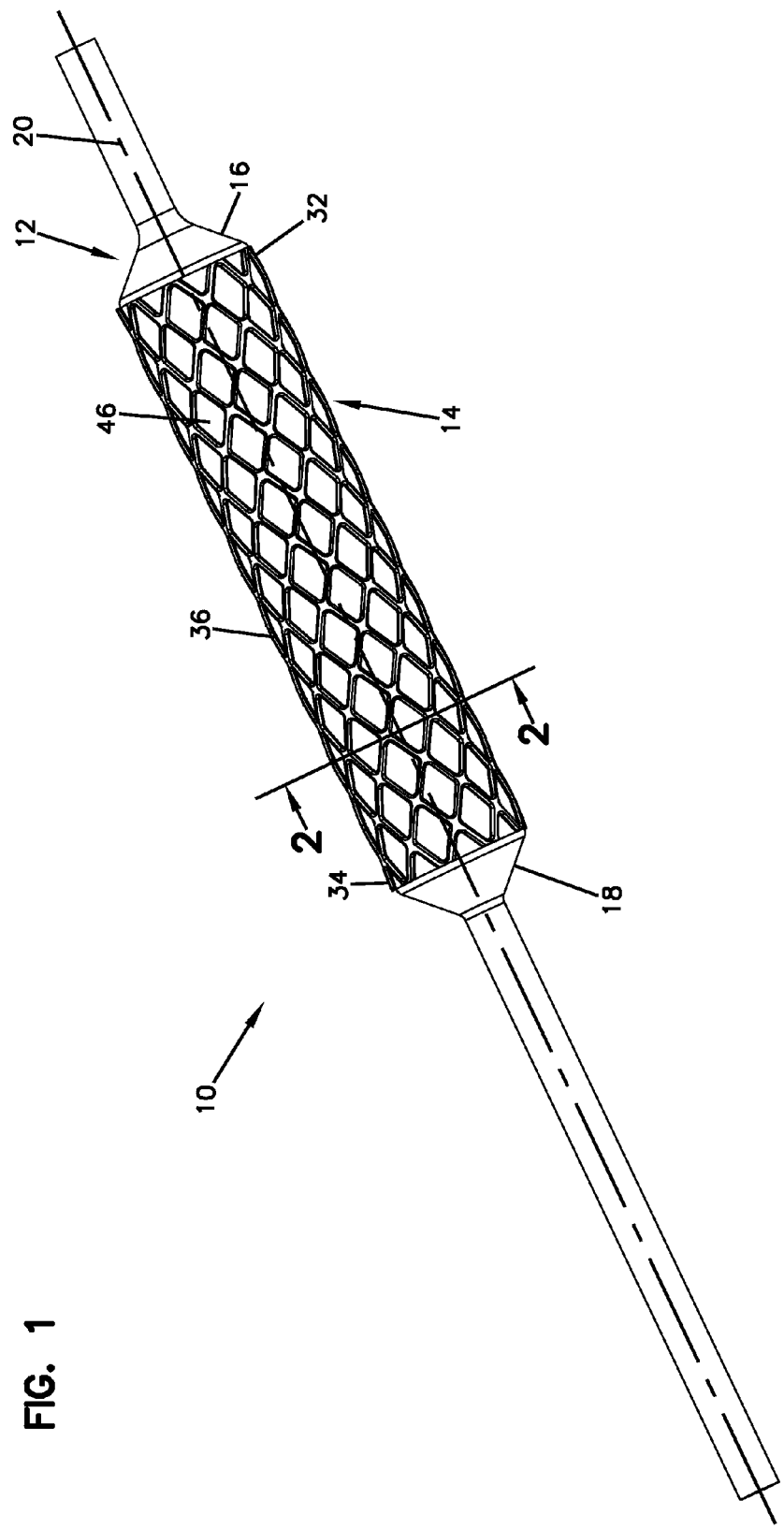
FIG. 1 is a side view of a catheter assembly having exemplary features of aspects in accordance with the principles of the present disclosure.

Referring now to FIG. 1, a catheter assembly 10 is shown. The catheter assembly 10 is adapted to provide a drug delivery system that protects a drug layer as the catheter assembly 10 is guided to a target site.

In the depicted embodiment, the catheter assembly 10 is adapted for use in medical procedures such as angioplasty. In an angioplasty procedure, the catheter assembly 10 is inserted into a blood vessel of a patient and guided to a target site in the vasculature of the patient. In one example, the target site is a location at which there is a blockage in a blood vessel that is restricting flow through that blood vessel.

In the subject embodiment, the catheter assembly 10 includes an expandable and collapsible structure 12 and a guard 14 that is bonded to the expandable and collapsible structure 12. In another embodiment, the guard 14 is held on the expandable and collapsible structure 12 by an inward radial force and/or friction.

The expandable and collapsible structure 12 of the catheter assembly 10 is expanded from a contracted state (shown in FIG. 1) to a dilated state (shown in FIG. 9) at the target site and subsequently collapsed from the dilated state to the contracted state. In one example, the dilation of the expandable and collapsible structure 12 compresses artheroma at the target site in the blood vessel. A coating disposed on the expandable and collapsible structure 12 is delivered to the tissue at or surrounding the target site when the expandable and collapsible structure 12 is in the dilated state. Referring now to the figures of the present disclosure, the catheter assembly 10 and the use of the catheter assembly 10 will be further described.

Figure 2:
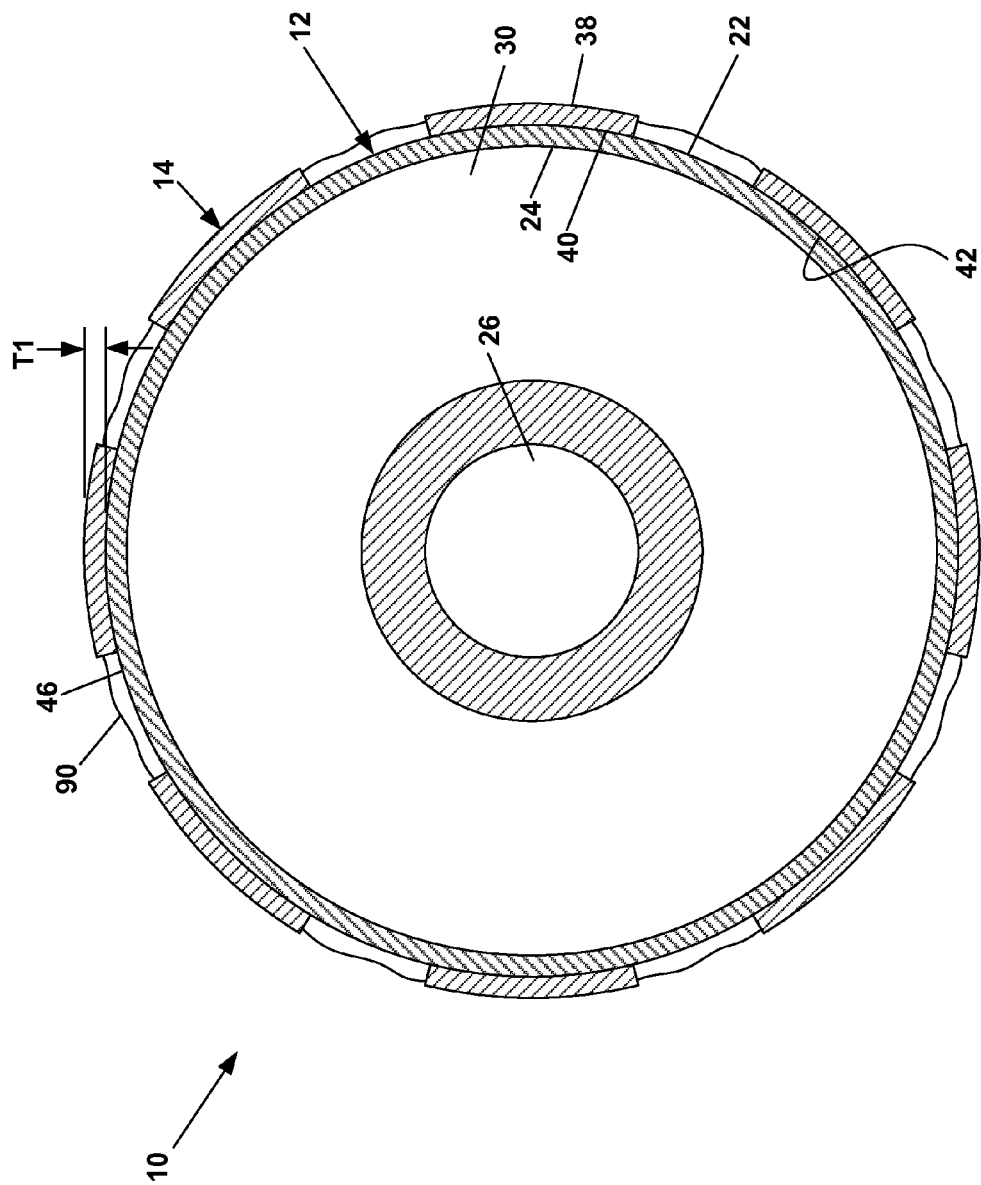
FIG. 2 is a cross-sectional view of the catheter assembly taken on line 2-2 of FIG. 1.
Figure 3:
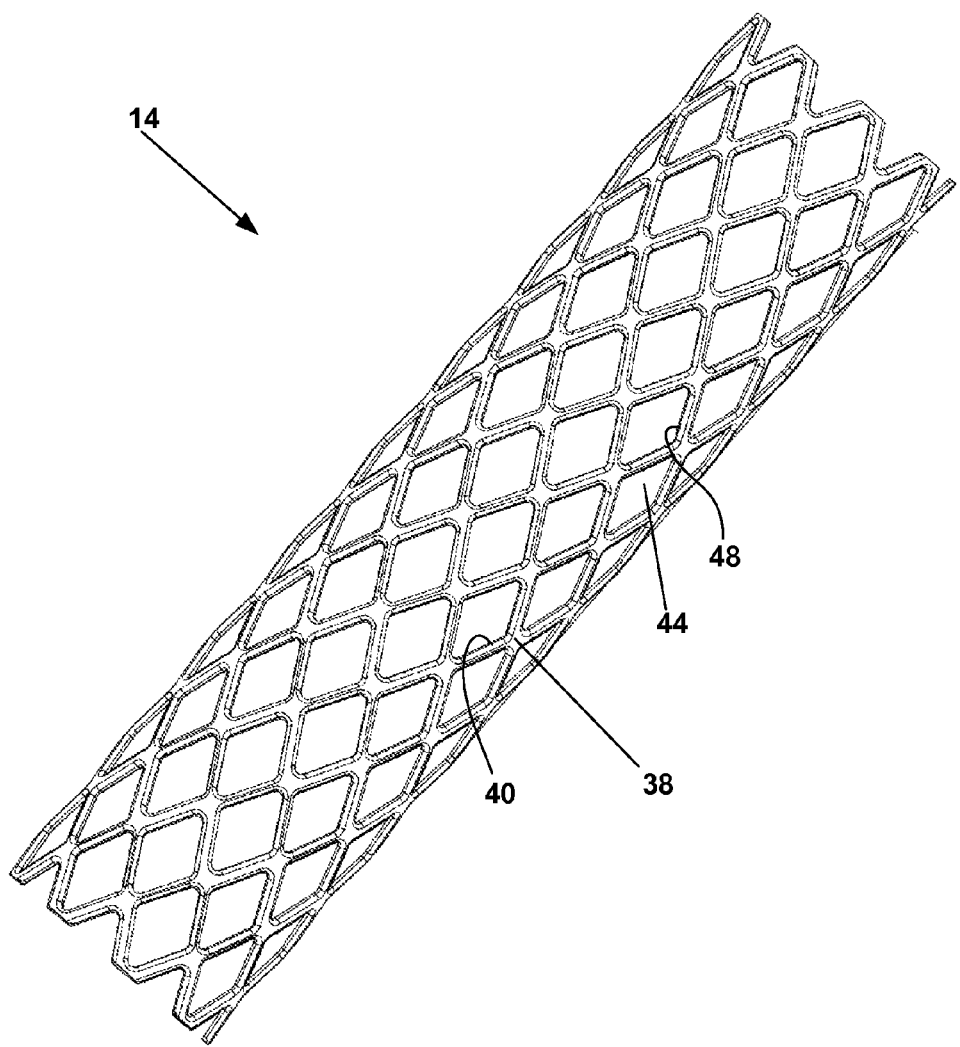
FIG. 3 is a perspective view of a guard suitable for use with the catheter assembly of FIG. 1.
Figure 4:
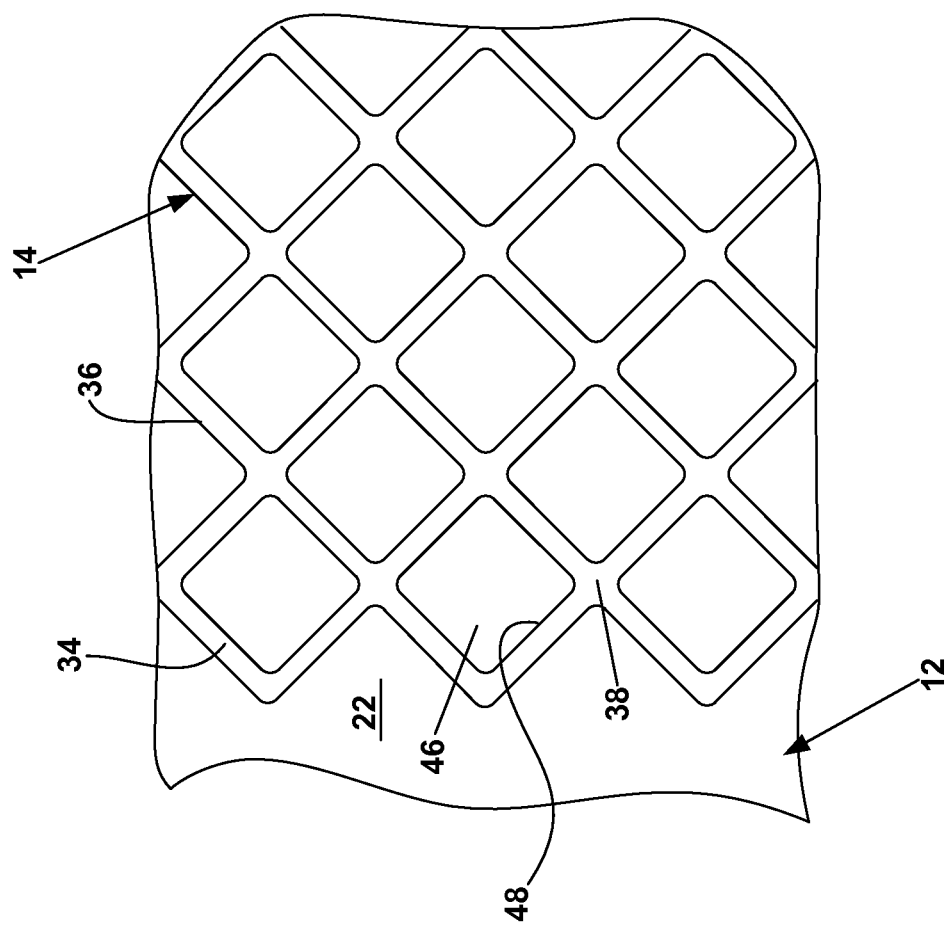
FIG. 4 is a fragmentary enlarged view of the guard and expandable and collapsible structure of the catheter assembly of FIG. 1.

Referring now to FIGS. 1 and 2, the expandable and collapsible structure 12 includes distal end 16 and a proximal end 18 and defines a central longitudinal axis 20 that extends through the distal and proximal ends 16, 18. The expandable and collapsible structure 12 has an outer surface 22 that extends between the distal and proximal ends 16, 18 and an oppositely disposed inner surface 24. The expandable and collapsible structure 12 further includes a guide passage 26 that extends through the distal and proximal ends 16 and 18. The guide passage 26 is adapted to receive a guide wire 28 (shown in FIG. 9) along which the catheter assembly 10 passes to the target site in the blood vessel of a body of the patient.

The expandable and collapsible structure 12 defines a lumen 30 disposed between the inner surface 24 of the expandable and collapsible structure 12 and the guide passage 26. The lumen 30 is adapted to receive a fluid (e.g., saline) to expand the expandable and collapsible structure 12 to the dilated state. When fluid is communicated to the lumen 30, the fluid exerts a radially outward force on the inner surface 24 of the expandable and collapsible structure 12. This radially outward force causes the expandable and collapsible structure 12 to dilate to the dilated state. When the fluid in the lumen 30 is drained, the expandable and collapsible structure 12 collapses or shrinks to the contracted state.

Referring now to FIGS. 1-4, the guard 14 will be described. The guard 14 is adapted for affixing to the expandable and collapsible structure 12. The guard 14 includes a first end 32 and an oppositely disposed second end 34. With the guard 14 fixedly mounted on the expandable and collapsible structure 12, the first end 32 of the guard 14 is disposed adjacent to the distal end 16 of the expandable and collapsible structure 12 while the second end 34 is disposed adjacent to the proximal end 18 of the expandable and collapsible structure 12.

The guard 14 further includes a plurality of rails 36 disposed between the first and second ends 32, 34. In the depicted embodiment, the plurality of rails is integrally connected so that the plurality of rails is monolithic. The rails 36 of the guard 14 include an exterior surface 38 and an oppositely disposed interior surface 40. The interior surface 40 defines a bore 42 that extends through the first and second ends 32, 34. The rails 36 of the guard 14 have a first thickness T1 that is equal to the radius of the exterior surface 38 minus the radius of the interior surface 40.

In the depicted embodiment, the guard 14 is fixed to the expandable and collapsible structure 12 so that the guard 14 does not move on the outer surface 22 of the expandable and collapsible structure 12. For example, the interior surface 40 of the guard 14 can be fixed on the outer surface 22 of the expandable and collapsible structure 12 so that the portions of the outer surface 22 of the expandable and collapsible structure 12 that are fixed to the interior surface 40 do not move relative to the guard 14. In an embodiment, the portions of the outer surface 22 of the expandable and collapsible structure 12 that are bonded to the interior surface 40 do not move in an axial direction relative to the guard 14.

The guard 14 defines a plurality of orifices 44 that extend through the exterior and interior surfaces 38, 40 of the guard 14. In one embodiment, the orifices 44 are generally shaped as a parallelogram. In another embodiment, the orifices 44 are generally shaped as a rhombus. It will be understood, however, that the scope of the disclosure is not limited to the orifices 44 being shaped as a parallelogram or rhombus as the orifices 44 could have various geometric shapes (e.g., rectangular, square, triangular, circular, etc.), and other shapes are illustrated in FIGS. 5 and 6.

The guard 14 and the outer surface 22 of the expandable and collapsible structure 12 cooperatively define a plurality of reservoirs 46. The guard 14 forms the sidewalls of the reservoir 46 while the expandable and collapsible structure 12 forms the base wall of the reservoir 46 so that each of the reservoirs 46 is bounded at its sides by the guard 14 and at its base by the expandable and collapsible structure 12. The reservoirs 46 are adapted to receive a coating that will be described in greater detail subsequently.

Each of the reservoirs 46 defines an opening 48. The opening 48 is disposed at the exterior surface 38 of the guard 14. The openings 48 of the reservoirs 46 are adapted to provide locations through which the coating can enter/exit the reservoirs 46.

Referring now to FIG. 5, an alternate embodiment of a guard 50 is shown. The guard 50 is adapted for affixing to the expandable and collapsible structure 12. The guard 50 includes a first end 52 and an oppositely disposed second end 54. With the guard 50 fixedly mounted on the expandable and collapsible structure 12, the first end 52 of the guard 50 is disposed adjacent to the distal end 16 of the expandable and collapsible structure 12 while the second end 54 is disposed adjacent to the proximal end 18 of the expandable and collapsible structure 12.

The guard 50 further includes a plurality of rails 56 disposed between the first and second ends 52, 54. In the depicted embodiment, the plurality of rails 56 is integrally connected so that the plurality of rails 56 is monolithic.

In the depicted embodiment of FIG. 5, the plurality of rails 56 includes a first plurality of rails 56a and a second plurality of rails 56b. The first plurality of rails 56a extends circumferentially around the outer surface 22 of the expandable and collapsible structure 12. In the depicted embodiment, the first plurality of rails 56a extends around the outer surface 22 of the expandable and collapsible structure 12 in a generally triangular wave-like pattern. The second plurality of rails 56b extends longitudinally along the outer surface 22 of the expandable and collapsible structure 12. In the depicted embodiment, the second plurality of rails 56b extends between the first and second ends 52, 54 of the guard 50.

The guard 50 is fixed on the expandable and collapsible structure 12 so that the guard 50 does not move on the outer surface 22 of the expandable and collapsible structure 12. For example, the guard 50 can be fixed on the outer surface 22 of the expandable and collapsible structure 12 so that the portions of the outer surface 22 of the expandable and collapsible structure 12 that are fixed to the guard 50 do not move relative to the guard 50.

The guard 50 defines a plurality of orifices 64 that extend through the guard 50. In the depicted embodiment, the orifices 64 are generally chevron shaped. It will be understood, however, that the scope of the disclosure is not limited to the orifices 64 being chevron shaped as the orifices 64 could have various geometric shapes (e.g., rectangular, square, triangular, circular, etc.), and other shapes are illustrated in FIGS. 1 and 6.

The guard 50 and the outer surface 22 of the expandable and collapsible structure 12 cooperatively define a plurality of reservoirs 66. The guard 50 forms the sidewalls of the reservoir 66 while the expandable and collapsible structure 12 forms the base wall of the reservoir 66 so that each of the reservoirs 66 is bounded at its sides by the guard 50 and at its base by the expandable and collapsible structure 12. The reservoirs 66 are adapted to receive a coating that will be described in greater detail subsequently.

Referring now to FIG. 6, an alternate embodiment of a guard 70 is shown. The guard 70 is adapted for affixing to the expandable and collapsible structure 12. The guard 70 includes a first end 72 and an oppositely disposed second end 74. With the guard 70 mounted on the expandable and collapsible structure 12, the first end 72 of the guard 70 is disposed adjacent to the distal end 16 of the expandable and collapsible structure 12 while the second end 74 is disposed adjacent to the proximal end 18 of the expandable and collapsible structure 12.

The guard 70 further includes a plurality of rails 76 disposed between the first and second ends 72, 74. In the depicted embodiment, the plurality of rails 76 extends circumferentially around the outer surface 22 of the expandable and collapsible structure 12. In the depicted embodiment, the plurality of rails 76 extends circumferentially around the expandable and collapsible structure 12 in a generally wave-like pattern. It will be understood, however, that the scope of the present disclosure is not limited to the plurality of rails 76 extending around the expandable and collapsible structure 12 in a wave-like pattern as the plurality of rails 76 can extend around the expandable and collapsible structure 12 in a straight line pattern or other pattern.

The guard 70 is fixed on the expandable and collapsible structure 12 so that the portions of the expandable and collapsible structure 12 that are fixed to the guard 50 do not move relative to the guard 50. In one embodiment, the guard 50 is thermally bonded to the expandable and collapsible structure 12. In another embodiment, the guard 50 is adhesively bonded to the expandable and collapsible structure 12.

The plurality of rails 76 and the expandable and collapsible structure 12 cooperatively define a plurality of reservoirs 78. The reservoirs 78 are adapted to receive the coating, which will be described in greater detail below. In the depicted embodiment, the reservoirs are channels that extend about the circumference of the expandable and collapsible structure 12.

Referring now to FIGS. 1 and 2, the expandable and collapsible structure 12 of the catheter assembly 10 is made of a first material. In an embodiment, the first material is a polymer or mixture of polymers. In an embodiment, the polymer is a polyethylene terephthalate. In an embodiment, the polymer is a nylon. The first material is a flexible material that is adapted to expand and collapse. In the depicted embodiment, the first material of the expandable and collapsible structure 12 includes a uniform thickness as measured by subtracting a radius of the outer surface 22 of the expandable and collapsible structure 12 from a radius of the inner surface 24.

The guard 14 is made of a second material. In an embodiment, the second material is different from the first material. The second material can be a polymer or mixture of polymers. In an embodiment, the polymer is a polytetrafluoroethylene, such as those sold under the trade name TEFLON®. In an embodiment, the second material is a nylon material. In an embodiment, the second material is less flexible than the first material. That is, when the expandable and collapsible structure expands, the first material expands but the second material does not expand or expands less than the first material. The first material can expand into and/or through the orifices defined by the second material. The expansion of the first material can push the coating out of the reservoirs (e.g., beyond the rails) to contact a tissue.

The second material of the guard 14 has the thickness T1 that is equal to the radius of the exterior surface 38 of the guard 14 minus the radius of the interior surface 40. The second material may be thicker than the first material. The second material is adapted to prevent the expandable and collapsible structure 12 from expanding at the interface between the expandable and collapsible structure 12 and the guard 14.

As described above the guard 14 is fixed to the expandable and collapsible structure 12. The guard 14 can be bonded to the expandable and collapsible structure 12. For example, the guard 14 can be thermally bonded to the outer surface 22 of the expandable and collapsible structure 12. In an embodiment, the first material is adhered to the second material. For example, adhesive (e.g., a layer of adhesive) can be disposed between the guard 14 and the expandable and collapsible structure 12. In an embodiment, the interior surface 40 of the guard 14 can be thermally or adhesively bonded to the outer surface 22 of the expandable and collapsible structure 12. In an embodiment, the guard 50 is thermally or adhesively bonded to the outer surface 22 of the expandable and collapsible structure 12.

Alternatively, the guard 14 and the expandable and collapsible structure 12 can be formed as an integral structure. That is, the guard 14 and the expandable and collapsible structure 12 can be made in such a way that the first material and the second material fuse, melt, crosslink, or cure to form a unitary structure. In an embodiment, the guard 14 is molded onto the expandable and collapsible structure 12. In an embodiment, the guard 14 is injection molded onto the expandable and collapsible structure 12. In an embodiment, the expandable and collapsible structure 12 and the guard 14 are manufactured using a multi-component injection molding process. In an embodiment, the expandable and collapsible structure 12 and the guard 14 are manufactured using a blow molding process.

In an embodiment, the guard 14 is affixed to the expandable and collapsible structure 12 using a 3D printing process.

Figure 7:
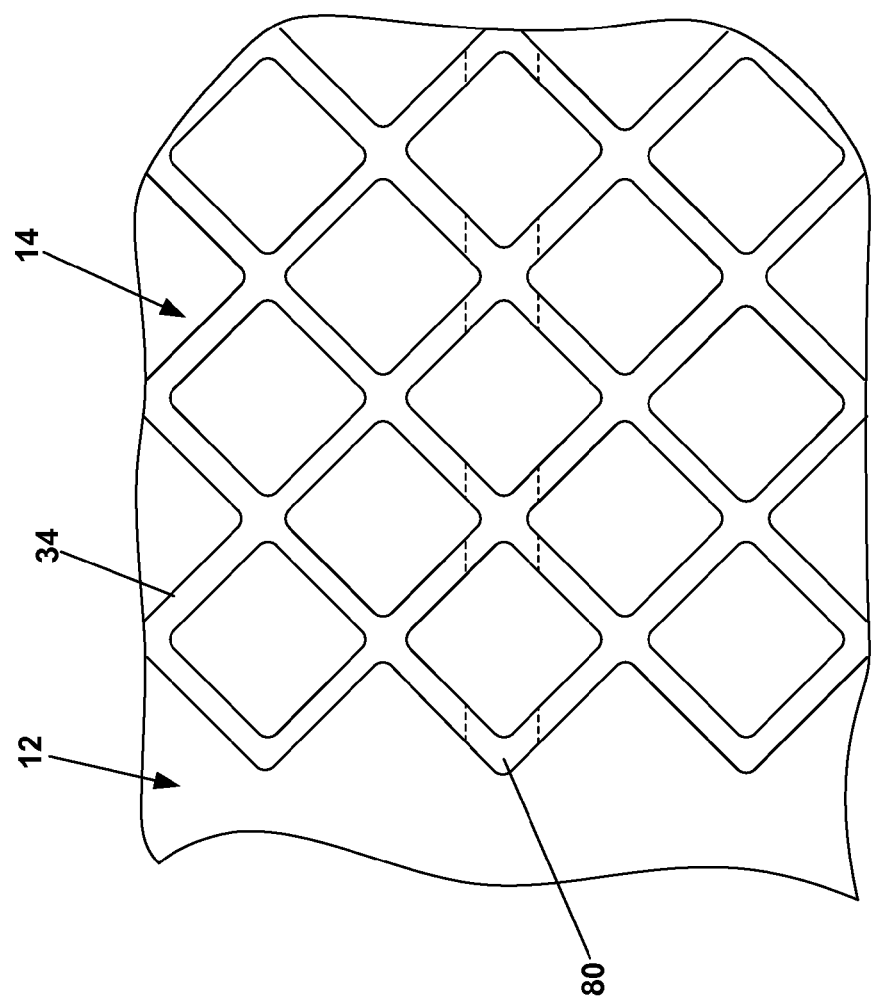
FIG. 7 is a fragmentary enlarged view of the guard and expandable and collapsible structure of the catheter assembly of FIG. 1.
Figure 8:
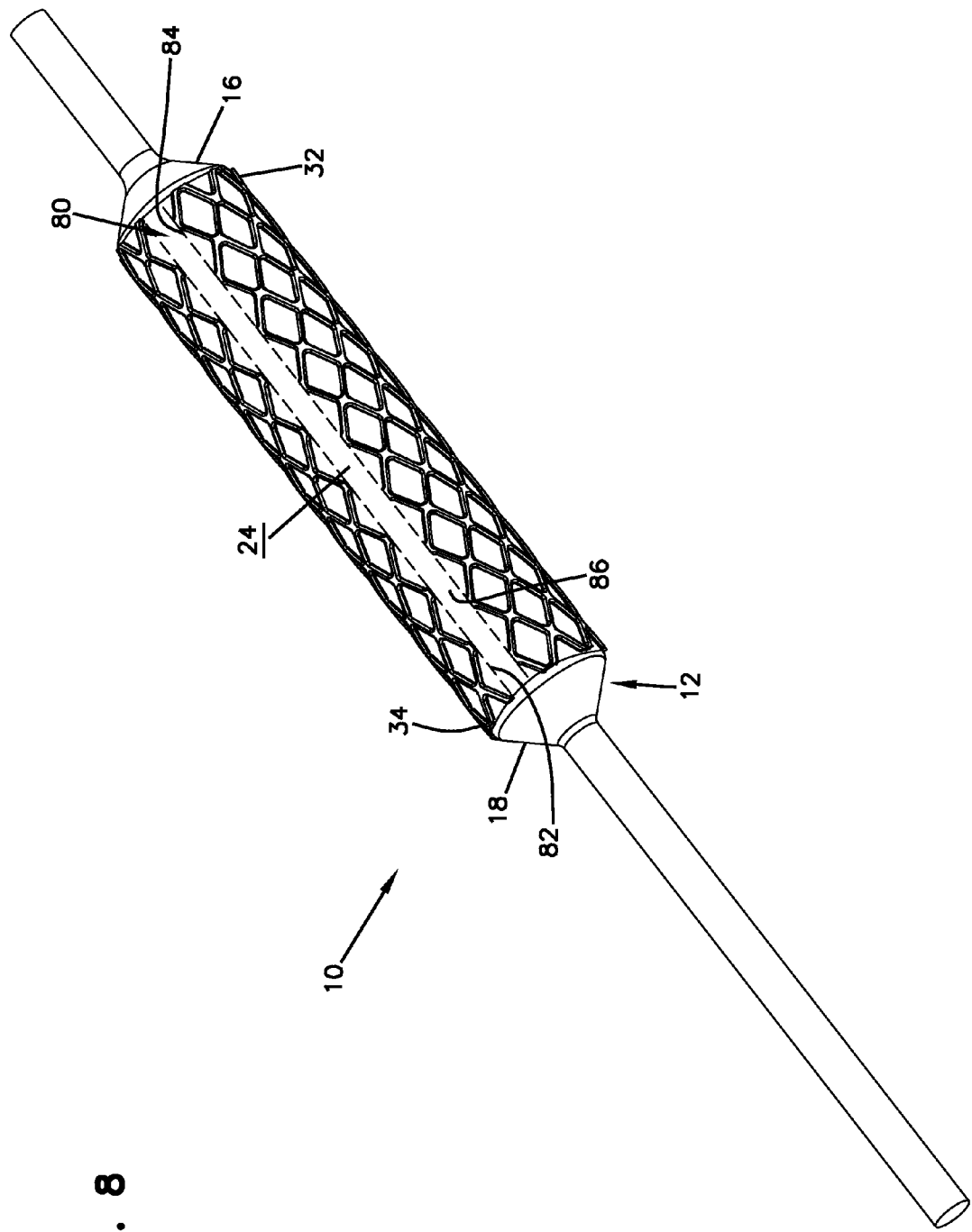
FIG. 8 is a perspective view of the guard and the expandable and collapsible structure of the catheter assembly of FIG. 1

Referring now to FIGS. 1, 7 and 8, the guard 14 includes a fold line 80. The fold line 80 extends from the first end 32 of the guard 14 to the second end 34. The fold line 80 includes a first edge 82 that extends between the first and second ends 32, 34 and an oppositely disposed second edge 84. While the guard 14 has the thickness T1 that is generally uniform, the thickness of the guard 14 between the first and second edges 82, 84 of the fold line 80 is reduced. This reduction in thickness at the fold line 80 allows the expandable and collapsible structure 12 to be more easily folded. In one embodiment, the guard 14 includes a plurality of fold lines 80. In another embodiment, the guard 14 includes two fold lines 80 that are disposed 180 degrees apart. In another embodiment, the guard 14 includes four fold lines 80, where each fold line 80 is 90 degrees from an immediately adjacent fold line 80.

In the depicted embodiment of FIG. 8, the first and second edges 82, 84 define a generally longitudinal groove 86 that extends between the first and second ends 32, 34 of the guard 14. The longitudinal groove 86 is uninterrupted and has the outer surface 24 of the expandable and collapsible structure 12 as a base wall. The guard 14 does not extend into the longitudinal groove 86 beyond the first and second edges 82, 84.

Coatings

Referring now to FIG. 2, the catheter assembly 10 can include any of a variety of coatings 90 including a bioactive agent. The coating 90 can be in one or more of the reservoirs 46 of the catheter assembly 10. Numerous suitable coatings and polymers useful in such coatings are described herein. Certain embodiments suitable for release of bioactive agent from the expandable and collapsible structure 12 can release effective amounts of the bioactive agent at the delivery site in seconds or minutes. The bioactive agent can be in an amorphous form incorporated into the coating or polymer matrix of the coating.

The coating 90 including the bioactive agent can be a flexible hydrogel matrix. The flexible hydrogel matrix can be made from a biostable hydrophilic polymer. The polymer can be covalently bonded to the expandable and collapsible structure. In some desired aspects, the biostable hydrophilic polymer is bonded to the surface of the expandable and collapsible structure via reacted photogroups.

The coating 90 including the bioactive agent can include a water-soluble polymer, for example, a water-soluble polymer such as poly(vinylpyrolidone). In some cases, the coating 90 includes a polymer that is covalently bonded to the surface of the expandable and collapsible structure via reacted photogroups. The coating 90 can also be formed from a composition in which the water-soluble polymer is in macromer form.

In an embodiment, at least a portion of the coating 90 including the bioactive agent is capable of becoming delaminated upon expansion of the expandable and collapsible structure in the subject. The delaminated biodegradable polymeric matrix with bioactive agent can, for example, adhere to the target tissue. Degradation of the delaminated polymeric matrix and release of the bioactive agent can occur at the target site. The biodegradable polymeric matrix can include the bioactive agent.

In an embodiment, the bioactive agent can be embedded in and/or attached to a fracturable, biodegradable coating that is present on the expandable and collapsible structure 12. In a non-expanded state, the bioactive material is substantially or entirely entrapped in the coating 90, or adhered to a coated layer, or both. Upon expansion of the expandable and collapsible structure 12, the coating fractures and delaminates from the outer surface 24 of the expandable and collapsible structure 12. Therefore, the coating can have properties of rigidity and brittleness. At the target site, portions of the coating are transferred to tissue along with the entrapped bioactive agent. In some cases the portions of the transferred coating can adhere to the tissue and provide a barrier or skin to improve its immobilization. Along with degradation of the biodegradable coating materials, bioactive agent can be released to provide a therapeutic effect.

A coating suitable for use as the coating 90 of the catheter assembly 10 has been described in U.S. patent application Ser. No. 61/360,212, entitled "Lipid Coating for Medical Devices Delivering Bioactive Agent," filed on Jun. 30, 2010 and having, the disclosure of which is hereby incorporated by reference in its entirety.

Coating Polymers

The coating can be formed from polymeric material (one or more polymers) that allows immobilization of the bioactive agent in a non-expanded state. The polymeric material can include one or more homopolymers, copolymers, combinations or blends thereof useful for forming the matrix. In an aspect, the polymeric material is used to form an flexible hydrogel matrix as the coating.

In some modes of preparation, a coating composition is formed that includes one or more matrix-forming polymer and bioactive agent. Gene7rally, the coating material is chosen and used in a composition suitable for forming a matrix with the bioactive agent. In one mode of practice, a hydrophilic polymer is used to prepare an aqueous composition that also includes the bioactive agent. The bioactive agent can be water insoluble, meaning that it does not readily dissolve in water.

Generally, a coating composition includes an amount and type of polymeric material that provides suitable physical properties (such as elasticity and bioactive agent retention). In some aspects the amount of polymeric material used to form the matrix in the composition is at a concentration in the range of about 5 mg/mL to about 50 mg/mL, about 10 mg/mL to about 40 mg/mL, or about 10 mg/mL to about 20 mg/mL. In an embodiment, the polymeric material is present in the coating composition at about 15 mg/mL.

The polymeric material can also include pendent photoreactive or polymerizable groups that can be activated to form a crosslinked matrix of polymer. The amount of polymer in the composition can also be chosen based on the level of derivatization with these groups.

One class of hydrophilic polymers useful as polymeric materials for matrix formation is synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these.

Examples of polymers that can be formed from these monomers include poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,N-dimethylacrylamide-co-aminopropylmethacrylamide) and poly(acrylamide-co-N,N-dimethylaminopropylmethacrylamide) are described in example 2 of U.S. Patent Pub. No. 2006/0030669 filed Sep. 17, 2004 (Taton et al.), the disclosure of which is incorporated herein by reference.

In some embodiments, the hydrophilic polymer is a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Patent Pub. No. 2006/0030669 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. This provides a hydrophilic polymer having a pendent activatable photogroup that can be applied to the expandable and collapsible structure, and then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Methods for the preparation of photo-polyacrylamide are described in U.S. Pat. No. 6,007,833, the disclosure of which is incorporated herein by reference.

In another embodiment, the polymers and copolymers as described are derivatized with one or more polymerizable group(s). Polymers with pendent polymerizable groups are commonly referred to macromers. The polymerizable group(s) can be present at the terminal portions (ends) of the polymeric strand or can be present along the length of the polymer. In one embodiment polymerizable groups are located randomly along the length of the polymer. Polymerizable groups can be activated form a crosslinked matrix in which the bioactive agent is immobilized.

Optionally, the coating can include a cross-linking agent. A crosslinking agent can promote the association of polymers in the coating, or the bonding of polymers to the surface of the expandable and collapsible structure. The choice of a particular crosslinking agent can depend on the ingredients of the coating composition.

Suitable crosslinking agents include two or more activatable groups, which can react with the polymers in the composition. Suitable activatable groups include photoreactive groups as described herein, like aryl ketones, such as acetophenone, benzophenone, anthraquinone, anthrone, quinone, and anthrone-like heterocycles.

The photoactivatable cross-linking agent can be ionic, and can have good solubility in an aqueous composition. Thus, in some embodiments, at least one ionic photoactivatable cross-linking agent is used to form the coating. The ionic cross-linking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable cross-linking agents include 4,5-bis(4-benzoylphenylmethyleneoxy) benzene-1, 3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis [2-(4-benzoylbenzyloxy)ethyl]-2-aminoethanesulfonic acid or salt, and the like. See U.S. Pat. No. 6,278,018, the disclosure of which is incorporated herein by reference.

Natural polymers can also be used to form the matrix. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In one mode of practice, the bioactive agent includes a first polymer that has a lower Tg than a second polymer. The second polymer, which is harder, can reduce the rate of release of the bioactive agent from the matrix. For example, the Tg of a suitable first polymer such as PLGA is about 45° C., and the Tg of a suitable second polymer such as PLLA is about 55° C. In some aspects the difference between the Tg of the first and second polymer is about 5° C. or greater. In more specific aspects the difference between the Tg of the first and second polymer is about 10° C. or greater. In some aspects, the first and second polymers have Tgs of about 35° C. or greater. In more specific aspects the first and second polymers have Tgs in the range of about 35° C. to about 65° C.

Selection of the first and second polymers can also be based on other properties of the polymers such as molecular weight, solubility, and rheology.

In certain embodiments, the polymer matrix includes an amphiphilic copolymer, a low molecular weight hydrophobic polymer, an organogel, a deformable hydrogel, a plurality thereof, or a mixture thereof. In an embodiment, the coating including a bioactive agent includes or is made of an amphiphilic copolymer. Suitable amphiphilic copolymers include a lactide/glycolide/caprolatone/polyethylene glycol copolymer. Such a copolymer can include blocks of polyethylene glycol. Although not limiting to the present disclosure, it is believed that an amphiphilic copolymer includes hydrophobic domains that enhance solubility of hydrophobic drugs and hydrophilic domains absorb water allowing the coating to swell upon exposure to blood.

In an embodiment, the coating including a bioactive agent includes or is made of a hydrophobic polymer of low average molecular weight. Suitable low molecular weight hydrophobic polymers include a polylactide/glycolide/caprolactone copolymer.

In an embodiment, the agent coating includes one or more solvents and the bioactive agent. In an embodiment, the agent coating includes an organogel. In an embodiment, the agent coating includes a deformable hydrogel.

In an embodiment, the agent coating includes a lipid. Although not limiting to the present disclosure it is believed that the lipid can enhance adhesion and penetration of drug into tissue. Drug can be emulsified into a lipid carrier.

In an embodiment, the drug is dissolved or dispersed in a deformable polymer layer, e.g., a hydrophobic polymer, an organogel, or a deformable hydrogel. In an embodiment, such a coating can flow or escape from the balloon surface and conform or adhere to the tissue upon expansion of the balloon.

Biodegradable Polymer

The biodegradable polymer can include one or more (e.g., 1, 2, 3 or 4) specific biodegradable polymers, for use in forming an implant in vivo. Suitable polymers will be biodegradable and will be substantially soluble in the biocompatible solvent system. Specifically, the biodegradable polymer can have a solubility of at least about 50 g/L in the biocompatible solvent system, at 25° C. and 1 atm. In one embodiment, the biodegradable polymer will not include a polymer that is substantially insoluble in the biocompatible solvent system. In an embodiment, the biodegradable polymer will not include a biodegradable polymer that is substantially insoluble in water or bodily fluids.

Suitable specific classes of polymers include, e.g., polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, block copolymers, multi-block co-polymers, multi-block co-polymers with polyethylene glycol (PEG), polyols, terpolymers and mixtures thereof.

In one embodiment, the biodegradable polymer is a thermoplastic polymer.

In one embodiment, the biodegradable polymer has a viscosity of at least about 100 cP at 37° C. In other embodiments, the biodegradable polymer has a viscosity of about 1,000 cP to about 30,000 cp at 37° C., about 5,000 cP to about 25,000 cp at 37° C., or about 10,000 cP to about 20,000 cp at 37° C.

In one embodiment, the biodegradable polymer is hydrophobic.

In one embodiment, the biodegradable polymer includes a block copolymer. In an embodiment, the biodegradable polymer is a polyethylene glycol (PEG) containing tri-block copolymer.

In one embodiment the polymer contains functional side groups.

The biodegradable polymer can be present in any suitable and effective amount, provided the biodegradable polymer is substantially soluble in the solvent system, and in combination with the solvent system will form an implant in vivo. In one embodiment, the biodegradable polymer is present in about 10 wt. % to about 40 wt. % of the formulation. In an embodiment, the biodegradable polymer is present in about 40 wt. % to about 90 wt. % of the formulation.

In one embodiment, the biodegradable polymer can include a poly(ether ester) multi-block copolymer, for example, that sold under the trade name SynBiosys™. In an embodiment, the biodegradable polymer can include a polyglycerol fatty acid ester. In an embodiment, the biodegradable polymer can include a PEG-PBT polymer. In an embodiment, the biodegradable polymer can include a poly(ester-amide) polymer (PEA). Poly(ether ester) Multi-Block Copolymers One suitable class of biodegradable polymers includes the poly(ether ester) multi-block copolymers. These multi-block copolymers are composed of various pre-polymer building blocks of different combinations of DL-lactide, glycolide, ε-caprolactone and polyethylene glycol. By varying the molecular composition, molecular weight (Mw 1200-6000) and ratio of the pre-polymer blocks, different functionalities can be introduced into the final polymer, which enables the creation of polymers with various physio-chemical properties. Both hydrophobic as well as hydrophilic/swellable polymers and slowly degrading as well as rapidly degrading polymers can be designed.

The poly(ether ester) multi-block copolymers can include a polymer as shown below (formula III):

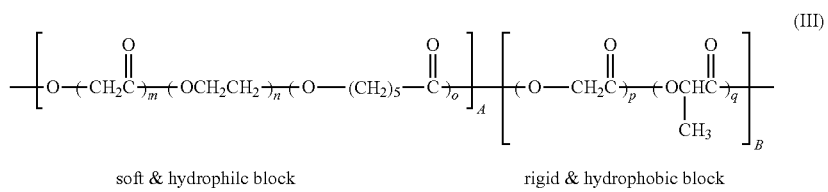

soft & hydrophile block      rigid & hydrophobic block wherein,
m and p are each independently glycolide;
n is polyethylene glycol, Mw 300-1000;
o is ε-caprolactone; and
q is DL-lactide.

Under physiological conditions, such poly(ether ester) multi-block copolymers can degrade completely via hydrolysis into non-toxic degradation products which are metabolized and/or excreted through the urinary pathway. Consequently, there can be no accumulation of biomaterials, thereby reducing the chance of long-term foreign body reactions.

Additional features and descriptions of the poly(ether ester) multi-block copolymers are provided, for example, in Published PCT Patent Application No. WO 2005/068533 and references cited therein. An overview is provided below.

The multi-block copolymers can specifically include two hydrolysable segments having a different composition, linked by a multifunctional, specifically an aliphatic chain-extender, and which are specifically essentially completely amorphous under physiological conditions (moist environment, body temperature, which is approximately 37° C. for humans).

The resulting multi-block copolymers can specifically have a structure according to any of the formulae (1)-(3):

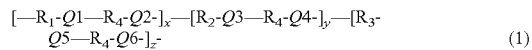

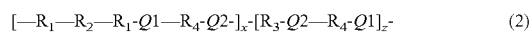

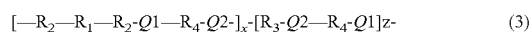

wherein:
$R_1$ and $R_2$ can be amorphous polyester, amorphous poly ether ester or amorphous polycarbonate; or an amorphous pre-polymer that is obtained from combined ester, ether and/or carbonate groups. $R_1$ and $R_2$ can contain polyether groups, which can result from the use of these compounds as a polymerization initiator, the polyether being amorphous or crystalline at room temperature. However, the polyether thus introduced will become amorphous at physiological conditions. $R_1$ and $R_2$ are derived from amorphous pre-polymers or blocks A and B, respectively, and $R_1$ and $R_2$ are not the same. $R_1$ and $R_2$ can contain a polyether group at the same time. In a specific embodiment, only one of them will contain a polyether group;

z is zero or a positive integer;

$R_3$ is a polyether, such as poly(ethylene glycol), and may be present (z≠0) or not (z=0). $R_3$ will become amorphous under physiological conditions;

$R_4$ is an aliphatic $C_2$-$C_8$ alkylene group, optionally substituted by a $C_1$-$C_{10}$ alkylene, the aliphatic group being linear or cyclic, wherein $R_4$ can specifically be a butylene, —$(CH_2)_4$- group, and the $C_1$-$C_{10}$ alkylene side group can contain protected S, N, P or O moieties;

x and y are both positive integers, which can both specifically be at least 1, whereas the sum of x and y (x+y) can specifically be at most 1000, more specifically at most 500, or at most 100. Q1-Q6 are linking units obtained by the reaction of the pre-polymers with the multifunctional chain-extender. Q1-Q6 are independently amine, urethane, amide, carbonate, ester or anhydride. The event that all linking groups Q are different being rare and not preferred.

Typically, one type of chain-extender can be used with three pre-polymers having the same end-groups, resulting in a copolymer of formula (1) with six similar linking groups. In case pre-polymers $R_1$ and $R_2$ are differently terminated, two types of groups Q will be present: e.g. Q1 and Q2 will be the same between two linked pre-polymer segments $R_1$, but Q1 and Q2 are different when $R_1$ and $R_2$ are linked. Obviously, when Q1 and Q2 are the same, it means that they are the same type of group but as mirror images of each other.

In copolymers of formula (2) and (3) the groups Q1 and Q2 are the same when two pre-polymers are present that are both terminated with the same end-group (which is usually hydroxyl) but are different when the pre-polymers are differently terminated (e.g. PEG which is diol terminated and a di-acid terminated 'tri-block' pre-polymer). In case of the tri-block pre-polymers ($R_1R_2R_1$ and $R_2R_1R_2$), the outer segments should be essentially free of PEG, because the coupling reaction by ring opening can otherwise not be carried out successfully. Only the inner block can be initiated by a PEG molecule.

The examples of formula (1), (2) and (3) show the result of the reaction with a di-functional chain-extender and di-functional pre-polymers.

With reference to formula (1) the polyesters can also be represented as multi-block or segmented copolymers having a structure (ab)n with alternating a and b segments or a structure (ab)r with a random distribution of segments a and b, wherein 'a' corresponds to the segment $R_1$ derived from pre-polymer (A) and 'b' corresponds to the segment $R_2$ derived from pre-polymer (B) (for z=0). In (ab)r, the a/b ratio (corresponding to x/y in formula (1)) may be unity or away from unity. The pre-polymers can be mixed in any desired amount and can be coupled by a multifunctional chain extender, viz. a compound having at least two functional groups by which it can be used to chemically link the pre-polymers. Specifically, this is a di-functional chain-extender. In case z≠0, then the presentation of a random distribution of all the segments can be given by (abc)r were three different pre-polymers (one being e.g. a polyethylene glycol) are randomly distributed in all possible ratio's. The alternating distribution is given by (abc)n. In this particular case, alternating means that two equally terminated pre-polymers (either a and c or b and c) are alternated with a differently terminated pre- polymer b or a, respectively, in an equivalent amount (a+c=b or b+c=a).

Those according to formula (2) or (3) have a structure (aba)n and (bab)n wherein the aba and bab 'triblock' pre-polymers are chain-extended with a di-functional molecule.

The method to obtain a copolymer with a random distribution of a and b (and optionally c) is far more advantageous than when the segments are alternating in the copolymer such as in (ab)n with the ratio of pre-polymers a and b being 1. The composition of the copolymer can then only be determined by adjusting the pre-polymer lengths. In general, the a and b segment lengths in (ab)n alternating copolymers are smaller than blocks in block-copolymers with structures ABA or AB.

The pre-polymers of which the a and b (and optionally c) segments are formed in (ab)r, (abc)r, (ab)n and (abc)n are linked by the di-functional chain-extender. This chain-extender can specifically be a diisocyanate chain-extender, but can also be a diacid or diol compound. In case all pre-polymers contain hydroxyl end-groups, the linking units will be urethane groups. In case (one of) the pre-polymers are carboxylic acid terminated, the linking units are amide groups. Multi-block copolymers with structure (ab)r and (abc)r can also be prepared by reaction of di-carboxylic acid terminated pre-polymers with a diol chain extender or vice versa (diol terminated pre-polymer with diacid chain-extender) using a coupling agent such as DCC (dicyclohexyl carbodiimide) forming ester linkages. In (aba)n and (bab)n the aba and bab pre-polymers are also specifically linked by an aliphatic di-functional chain-extender, more specifically, a diisocyanate chain-extender.

The term "randomly segmented" copolymers refers to copolymers that have a random distribution (i.e. not alternating) of the segments a and b: (ab)r or a, b and c: (abc)r.

PEG-PBT polymers

One suitable class of biodegradable polymers includes the poly(ether ester) multiblock copolymers based on poly(ethylene glycol) (PEG) and poly(butylene terephthalate) (PBT), that can be described by the following general formula IV:

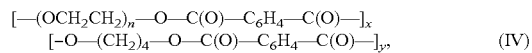

$$[—(OCH_2CH_2)_n—O—C(O)—C_6H_4—C(O)—]_x$$
$$[-O—(CH_2)_4—O—C(O)—C_6H_4—C(O)—]_y, \quad (IV)$$

wherein,

—$C_6H_4$- designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer.

In specific embodiments, n can be selected such that the molecular weight of the PEG block is between about 300 and about 4000. In specific embodiments, x and y can each be independently selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and bioactive agent release characteristics (e.g., through controlled polymer degradation and swelling) by varying the values of n, x and y in the copolymer structure.

Polyester Amides

One suitable class of biodegradable polymers includes the polyesteramide polymers having a subunit of the formula (V):

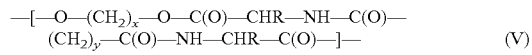

$$—[—O—(CH_2)_x—O—C(O)—CHR—NH—C(O)—$$
$$(CH_2)_y—C(O)—NH—CHR—C(O)—]— \quad (V)$$

wherein, x is $C_2$-$C_{12}$, y is $C_2$-$C_{12}$, and

R is —$CH(CH_3)_2$, —$CH_2CH(CH_3)_2$, —$CH(CH_3)$ $CH_2CH_3$, —$CH_2(CH_2)_2CH_3$, —$CH_2C_6H_5$, —$CH_2(CH_2)_2$ $SCH_3$ or part of an amino acid.

In specific embodiments, the $C_2$-$C_{12}$ can be ($C_2$-$C_{12}$) alkyl. In other specific embodiments, the $C_2$-$C_{12}$ can be ($C_2$-$C_{12}$) alkyl, optionally substituted.

Such polymers are described, for example, in U.S. Pat. No. 6,703,040. Polymers of this nature can be described with a nomenclature of x-aa-y, wherein "x" represents an alkyl diol with x carbon atoms, "aa" represents an amino acid such as leucine or phenylalanine, and y represents an alkyldicarboxylic acid with y carbon atoms, and wherein the polymer is a polymerization of the diol, the dicarboxylic acid, and the amino acid. An exemplary polymer of this type is 4-Leu-4.

Poly(ester-amide)polymer (PEA)

One suitable class of biodegradable polymers includes the poly(ester-amide) polymers. Such polymers can be prepared by polymerization of a diol, a dicarboxylic acid and an alpha-amino acid through ester and amide links in the form $(DACA)_n$. An example of a $(DACA)_n$ polymer is shown below in formula VI. Suitable amino acids include any natural or synthetic alpha-amino acids, specifically neutral amino acids.

Diols can be any aliphatic diol, including alkylene diols like HO—$(CH_2)_k$—OH (i.e. non-branched), branched diols (e.g., propylene glycol), cyclic diols (e.g. dianhydrohexitols and cyclohexanediol), or oligomeric diols based on ethylene glycol (e.g., diethylene glycol, triethylene glycol, tetraethylene glycol, or poly(ethylene glycol)s). Aromatic diols (e.g., bis-phenols) are less useful for these purposes since they are more toxic, and polymers based on them have rigid chains that are less likely to biodegrade.

Dicarboxylic acids can be any aliphatic dicarboxylic acid, such as α-omega-dicarboxylic acids (i.e., non-branched), branched dicarboxylic acids, cyclic dicarboxylic acids (e.g. cyclohexanedicarboxylic acid). Aromatic diacids (like phthalic acids, etc.) are less useful for these purposes since they are more toxic, and polymers based on them have rigid chain structure, exhibit poorer film-forming properties and have much lower tendency to biodegrade.

Specific PEA polymers have the formula VI:

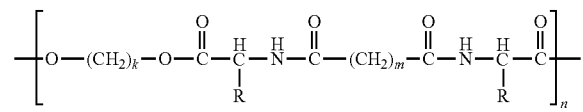

(VI)

wherein, k is 2-12 (e.g., 2, 3, 4, or 6);

m is 2-12 (e.g., 4 or 8); and

R is —$CH(CH_3)_2$, —$CH_2CH(CH_3)_2$, —$CH(CH_3)$ $CH_2CH_3$, —$CH_2(CH_2)_2CH_3$, —$CH_2(C_6H_5)$, or —$CH_2(CH_2)SH_3$.

In specific embodiments, A is L-phenylalanine (Phe-PEA) and A is L-leucine (Leu-PEA). In specific embodiments, the ratio of Phe-PEA to Leu-PEA is from 10:1 to 1:1. In other specific embodiments, the ratio of Phe-PEA to Leu-PEA is from 5:1 to 2.5:1.

Additional features and descriptions of the poly(ester-amide) polymers (PEA) are provided, for example, in U.S. Pat. No. Re40,359, which is a reissue of U.S. Pat. No. 6,703,040.

Hydrophobic Derivatives of Natural Biodegradable Polysaccharides

One suitable class of biodegradable polymers includes the hydrophobic derivatives of natural biodegradable polysaccharides, such as those sold under the trade name Eureka™ SOLO polymers. Hydrophobic derivatives of natural biodegradable polysaccharide refer to a natural biodegradable polysaccharide having one or more hydrophobic pendent groups attached to the polysaccharide. In many cases the hydrophobic derivative includes a plurality of groups that include hydrocarbon segments attached to the polysaccharide. When a plurality of groups including hydrocarbon segments are attached, they are collectively referred to as the "hydrophobic portion" of the hydrophobic derivative. The hydrophobic derivatives therefore include a hydrophobic portion and a polysaccharide portion.

The polysaccharide portion includes a natural biodegradable polysaccharide, which refers to a non-synthetic polysaccharide that is capable of being enzymatically degraded. Natural biodegradable polysaccharides include polysaccharide and/or polysaccharide derivatives that are obtained from natural sources, such as plants or animals. Natural biodegradable polysaccharides include any polysaccharide that has been processed or modified from a natural biodegradable polysaccharide (for example, maltodextrin is a natural biodegradable polysaccharide that is processed from starch). Exemplary natural biodegradable polysaccharides include maltodextrin, amylose, cyclodextrin, polyalditol, hyaluronic acid, dextran, heparin, chondroitin sulfate, dermatan sulfate, heparan sulfate, keratan sulfate, dextran, dextran sulfate, pentosan polysulfate, and chitosan. Specific polysaccharides are low molecular weight polymers that have little or no branching, such as those that are derived from and/or found in starch preparations, for example, maltodextrin, amylose, and cyclodextrin. Therefore, the natural biodegradable polysaccharide can be a substantially non-branched or completely non-branched poly(glucopyranose) polymer.

"Amylose" or "amylose polymer" refers to a linear polymer having repeating glucopyranose units that are joined by α-1,4 linkages. Some amylose polymers can have a very small amount of branching via α-1,6 linkages (about less than 0.5% of the linkages) but still demonstrate the same physical properties as linear (unbranched) amylose polymers do. Generally amylose polymers derived from plant sources have molecular weights of about $1 \times 10^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of $1 \times 10^7$ Da or greater.

For example, in some aspects, starch preparations having a high amylose content, purified amylose, synthetically prepared amylose, or enriched amylose preparations can be used in the preparation of a hydrophobic derivative of amylose. In starch sources, amylose is typically present along with amylopectin, which is a branched polysaccharide. If a mixture of amylose and a higher molecular weight precursor is used (such as amylopectin), amylose can be present in the composition in an amount greater than the higher molecular weight precursor. For example, in some aspects, starch preparations having high amylose content, purified amylose, synthetically prepared amylose, or enriched amylose preparations can be used in the preparation of a hydrophobic derivative of amylose polymer. In some embodiments the composition includes a mixture of polysaccharides including amylose wherein the amylose content in the mixture of polysaccharides is 50% or greater, 60% or greater, 70% or greater, 80% or greater, or 85% or greater by weight. In other embodiments the composition includes a mixture of polysaccharides including amylose and amylopectin and wherein the amylopectin content in the mixture of polysaccharides is 30% or less, or 15% or less.

The amount of amylopectin present in a starch may also be reduced by treating the starch with amylopectinase, which cleaves α-1,6 linkages resulting in the debranching of amylopectin into amylose.

Steps may be performed before, during, and/or after the process of derivatizing the amylose polymer with a pendent group comprising a hydrocarbon segment to enrich the amount of amylose, or purify the amylose.

Amylose of particular molecular weights can be obtained commercially or can be prepared. For example, synthetic amyloses with average molecular masses of 70 kDa, 110 kDa, and 320 kDa, can be obtained from Nakano Vinegar Co., Ltd. (Aichi, Japan). The decision of using amylose of a particular size range may depend on factors such as the physical characteristics of the composition (e.g., viscosity), the desired rate of degradation of the implant, and the nature and amount of the active pharmaceutical ingredient (API).

Purified or enriched amylose preparations can be obtained commercially or can be prepared using standard biochemical techniques such as chromatography. In some aspects, high-amylose cornstarch can be used to prepare the hydrophobic derivative.

Maltodextrin is typically generated by hydrolyzing a starch slurry with heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate X 100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights, for example, in the range of about 500 Da to 5000 Da are commercially available (for example, from CarboMer, San Diego, Calif.).

Another contemplated class of natural biodegradable polysaccharides is natural biodegradable non-reducing polysaccharides. A non-reducing polysaccharide can provide an inert matrix thereby improving the stability of active pharmaceutical ingredients (APIs), such as proteins and enzymes. A non-reducing polysaccharide refers to a polymer of non-reducing disaccharides (two monosaccharides linked through their anomeric centers) such as trehalose (α-D-glucopyranosyl α-D-glucopyranoside) and sucrose (β-D-fructofuranosyl α-D-glucopyranoside). An exemplary non-reducing polysaccharide includes polyalditol which is available from GPC (Muscatine, Iowa). In another aspect, the polysaccharide is a glucopyranosyl polymer, such as a polymer that includes repeating (1→3)O-β-D-glucopyranosyl units.

Dextran is an α-D-1,6-glucose-linked glucan with side-chains 1-3 linked to the backbone units of the dextran biopolymer. Dextran includes hydroxyl groups at the 2, 3, and 4 positions on the glucopyranose monomeric units. Dextran can be obtained from fermentation of sucrose-containing media by Leuconostoc mesenteroides B512F.

Dextran can be obtained in low molecular weight preparations. Enzymes (dextranases) from molds such as Penicillium and Verticillium have been shown to degrade dextran. Similarly many bacteria produce extracellular dextranases that split dextran into low molecular weight sugars.

Chondroitin sulfate includes the repeating disaccharide units of D-galactosamine and D-glucuronic acid, and typically contains between 15 to 150 of these repeating units. Chondroitinase AC cleaves chondroitin sulfates A and C, and chondroitin.

Hyaluronic acid (HA) is a naturally derived linear polymer that includes alternating β-1,4-glucuronic acid and β-1,3-N-acetyl-D-glucosamine units. HA is the principal glycosaminoglycan in connective tissue fluids. HA can be fragmented in the presence of hyaluronidase.

In many aspects the polysaccharide portion and the hydrophobic portion include the predominant portion of the hydrophobic derivative of the natural biodegradable polysaccharide. Based on a weight percentage, the polysaccharide portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. Likewise, based on a weight percentage of the overall hydrophobic derivative, the hydrophobic portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. In exemplary aspects, the hydrophobic derivative has approximately 50% of its weight attributable to the polysaccharide portion, and approximately 50% of its weight attributable to its hydrophobic portion.

The hydrophobic derivative has the properties of being insoluble in water. The term for insolubility is a standard term used in the art, and meaning 1 part solute per 10,000 parts or greater solvent. (see, for example, Remington: The Science and Practice of Pharmacy, 20th ed. (2000), Lippincott Williams & Wilkins, Baltimore Md.).

A hydrophobic derivative can be prepared by associating one or more hydrophobic compound(s) with a natural biodegradable polysaccharide polymer. Methods for preparing hydrophobic derivatives of natural biodegradable polysaccharides are described herein.

The hydrophobic derivatives of the natural biodegradable polysaccharides specifically have an average molecular weight of up to about 1,000,000 Da, up to about 300,000 Da or up to about 100,000 Da. Use of these molecular weight derivatives can provide implants with desirable physical and drug-releasing properties. In some aspects the hydrophobic derivatives have a molecular weight of about 250,000 Da or less, about 100,000 Da or less, about 50,000 Da or less, or 25,000 Da or less. Particularly specific size ranges for the natural biodegradable polysaccharides are in the range of about 2,000 Da to about 20,000 Da, or about 4,000 Da to about 10,000 Da.

The molecular weight of the polymer is more precisely defined as "weight average molecular weight" or $M_w$. $M_w$ is an absolute method of measuring molecular weight and is particularly useful for measuring the molecular weight of a polymer (preparation). Polymer preparations typically include polymers that individually have minor variations in molecular weight. Polymers are molecules that have a relatively high molecular weight and such minor variations within the polymer preparation do not affect the overall properties of the polymer preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W. (1990) *Contemporary Polymer Chemistry*; pg 271.

The addition of hydrophobic portion will generally cause an increase in molecular weight of the polysaccharide from its underivatized, starting molecular weight. The amount increase in molecular weight can depend on one or more factors, including the type of polysaccharide derivatized, the level of derivation, and, for example, the type or types of groups attached to the polysaccharide to provide the hydrophobic portion.

In some aspects, the addition of hydrophobic portion causes an increase in molecular weight of the polysaccharide of about 20% or greater, about 50% or greater, about 75% or greater, about 100% or greater, or about 125%, the increase in relation to the underivatized form of the polysaccharide.

As an example, a maltodextrin having a starting weight of about 3000 Da is derivatized to provide pendent hexanoate groups that are coupled to the polysaccharide via ester linkages to provide a degree of substitution (DS) of about 2.5. This provides a hydrophobic polysaccharide having a theoretical molecular weight of about 8400 Da.

In forming the hydrophobic derivative of the natural biodegradable polysaccharide and as an example, a compound having a hydrocarbon segment can be covalently coupled to one or more portions of the polysaccharide. For example, the compound can be coupled to monomeric units along the length of the polysaccharide. This provides a polysaccharide derivative with one or more pendent groups. Each chemical group includes a hydrocarbon segment. The hydrocarbon segment can constitute all of the pendent chemical group, or the hydrocarbon segment can constitute a portion of the pendent chemical group. For example, a portion of the hydrophobic polysaccharide can have the following structural formula (I):

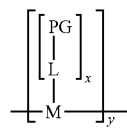

(I)

wherein each M is independently a monosaccharide unit, each L is independently a suitable linking group, or is a direct bond, each PG is independently a pendent group, each x is independently 0 to about 3, such that when x is 0, the bond between L and M is absent, and y is 3 or more.

Additionally, the polysaccharide that includes the unit of formula (I) above can be a compound of formula (II):

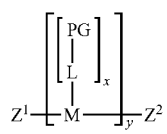

(II)

wherein each M is independently a monosaccharide unit, each L is independently a suitable linking group, or is a direct bond, each PG is independently a pendent group, each x is independently 0 to about 3, such that when x is 0, the bond between L and M is absent, y is about 3 to about 5,000, and $Z^1$ and $Z^2$ are each independently hydrogen, $OR^1$, $OC(=O)R^1$, $CH_2OR^1$, $SiR^1$ or $CH_2OC(=O)R^1$. Each $R^1$ is independently hydrogen, alkyl, cycloalkyl, cycloalkyl alkyl, aryl, aryl alkyl, heterocyclyl or heteroaryl, each alkyl, cycloalkyl, aryl, heterocycle and heteroaryl is optionally substituted, and each alkyl, cycloalkyl and heterocycle is optionally partially unsaturated.

For the compounds of formula (I) and (II), the monosaccharide unit (M) can include D-glucopyranose (e.g., α-D-glucopyranose). Additionally, the monosaccharide unit (M) can include non-macrocyclic poly-α(1→4) glucopyranose, non-macrocyclic poly-α(1→6) glucopyranose, or a mixture or combination of both non-macrocyclic poly-α(1→4) glucopyranose and non-macrocyclic poly-α(1→6) glucopyranose. For example, the monosaccharide unit (M) can include glucopyranose units, wherein at least about 90% are linked by α(1→4) glycosidic bonds. Alternatively, the monosaccharide unit (M) can include glucopyranose units, wherein at least about 90% are linked by α(1→6) glycosidic bonds. Additionally, each of the monosaccharides in the polysaccharide can be the same type (homopolysaccharide), or the monosaccharides in the polysaccharide can differ (heteropolysaccharide).

The polysaccharide can include up to about 5,000 monosaccharide units (i.e., y in the formula (I) or (II) is up to 5,000). Specifically, the monosaccharide units can be glucopyranose units (e.g., α-D-glucopyranose units). Additionally, y in the formula (I) or (II) can specifically be about 3-5,000 or about 3-4,000 or about 100 to 4,000.

In specific embodiments, the polysaccharide is non-macrocyclic. In other specific embodiments, the polysaccharide is linear. In other specific embodiments, the polysaccharide is branched. In yet further specific embodiments, the polysaccharide is a natural polysaccharide (PS).

The polysaccharide will have a suitable glass transition temperature (Tg). In one embodiment, the polysaccharide will have a glass transition temperature (Tg) of at least about 35° C. (e.g., about 40° C. to about 150° C.). In an embodiment, the polysaccharide will have a glass transition temperature (Tg) of −30° C. to about 0° C.

A "pendant group" refers to a group of covalently bonded carbon atoms having the formula $(CH_n)_m$, wherein m is 2 or greater, and n is independently 2 or 1. A hydrocarbon segment can include saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups. Specifically, the pendant group includes linear, straight chain or branched $C_1$-$C_{20}$ alkyl group; an amine terminated hydrocarbon or a hydroxyl terminated hydrocarbon. In an embodiment, the pendant group includes polyesters such as polylactides, polyglycolides, poly(lactide-co-glycolide) co-polymers, polycaprolactone, terpolymers of poly(lactide-co-glycolide-co-caprolatone), or combinations thereof.

The monomeric units of the hydrophobic polysaccharides described herein typically include monomeric units having ring structures with one or more reactive groups. These reactive groups are exemplified by hydroxyl groups, such as the ones that are present on glucopyranose-based monomeric units, e.g., of amylose and maltodextrin. These hydroxyl groups can be reacted with a compound that includes a hydrocarbon segment and a group that is reactive with the hydroxyl group (a hydroxyl-reactive group).

Examples of hydroxyl reactive groups include acetal, carboxyl, anhydride, acid halide, and the like. These groups can be used to form a hydrolytically cleavable covalent bond between the hydrocarbon segment and the polysaccharide backbone. For example, the method can provide a pendent group having a hydrocarbon segment, the pendent group linked to the polysaccharide backbone with a cleavable ester bond. In these aspects, the synthesized hydrophobic derivative of the natural biodegradable polysaccharide can include chemical linkages that are both enzymatically cleavable (the polymer backbone) and non-enzymatically hydrolytically cleavable (the linkage between the pendent group and the polymer backbone).

Other cleavable chemical linkages (e.g., metabolically cleavable covalent bonds) that can be used to bond the pendent groups to the polysaccharide include carboxylic ester, carbonate, borate, silyl ether, peroxyester groups, disulfide groups, and hydrazone groups.

In some cases, the hydroxyl reactive groups include those such as isocyanate and epoxy. These groups can be used to form a non-cleavable covalent bond between the pendent group and the polysaccharide backbone. In these aspects, the synthesized hydrophobic derivative of the natural biodegradable polysaccharide includes chemical linkages that are enzymatically cleavable.

Other reactive groups, such as carboxyl groups, acetyl groups, or sulphate groups, are present on the ring structure of monomeric units of other natural biodegradable polysaccharides, such as chondrotin or hyaluronic acid. These groups can also be targeted for reaction with a compound having a hydrocarbon segment to be bonded to the polysaccharide backbone.

Various factors can be taken into consideration in the synthesis of the hydrophobic derivative of the natural biodegradable polysaccharide. These factors include the physical and chemical properties of the natural biodegradable polysaccharide, including its size, and the number and presence of reactive groups on the polysaccharide and solubility, the physical and chemical properties of the compound that includes the hydrocarbon segment, including its the size and solubility, and the reactivity of the compound with the polysaccharide.

In preparing the hydrophobic derivative of the natural biodegradable polysaccharide any suitable synthesis procedure can be performed. Synthesis can be carried out to provide a desired number of groups with hydrocarbon segments pendent from the polysaccharide backbone. The number and/or density of the pendent groups can be controlled, for example, by controlling the relative concentration of the compound that includes the hydrocarbon segment to the available reactive groups (e.g., hydroxyl groups) on the polysaccharide.

The type and amount of groups having the hydrocarbon segment pendent from the polysaccharide is sufficient for the hydrophobic polysaccharide to be insoluble in water. In order to achieve this, as a general approach, a hydrophobic polysaccharide is obtained or prepared wherein the groups having the hydrocarbon segment pendent from the polysaccharide backbone in an amount in the range of 0.25 (pendent group): 1 (polysaccharide monomer) by weight.

The weight ratio of glucopyranose units to pendent groups can vary, but will typically be about 1:1 to about 100:1. Specifically, the weight ratio of glucopyranose units to pendent groups can be about 1:1 to about 75:1, or about 1:1 to about 50:1. Additionally, the nature and amount of the pendent group can provide a suitable degree of substitution to the polysaccharide. Typically, the degree of substitution will be in the range of about 0.1-5 or about 0.5-2.

To exemplify these levels of derivation, very low molecular weight (less than 10,000 Da) glucopyranose polymers are reacted with compounds having the hydrocarbon segment to provide low molecular weight hydrophobic glucopyranose polymers. In one mode of practice, the natural biodegradable polysaccharide maltodextrin in an amount of 10 g (MW 3000-5000 Da; ~3 mmols) is dissolved in a suitable solvent, such as tetrahydrofuran. Next, a solution having butyric anhydride in an amount of 18 g (0.11 mols) is added to the maltodextrin solution. The reaction is allowed to proceed, effectively forming pendent butyrate groups on the pyranose rings of the maltodextrin polymer. This level of derivation results in a degree of substitution (DS) of butyrate group of the hydroxyl groups on the maltodextrin of about 1.

For maltodextrin and other polysaccharides that include three hydroxyl groups per monomeric unit, on average, one of the three hydroxyl groups per glycopyranose monomeric unit becomes substituted with a butyrate group. A maltodextrin polymer having this level of substitution is referred to herein as maltodextrin-butyrate DS 1. As described herein, the DS refers to the average number of reactive groups (including hydroxyl and other reactive groups) per monomeric unit that are substituted with pendent groups comprising hydrocarbon segments.

An increase in the DS can be achieved by incrementally increasing the amount of compound that provides the hydrocarbon segment to the polysaccharide. As another example, butyrylated maltodextrin having a DS of 2.5 is prepared by reacting 10 g of maltodextrin (MW 3000-5000 Da; ~3 mmols) with 0.32 mols butyric anhydride.

The degree of substitution can influence the hydrophobic character of the polysaccharide. In turn, implants formed from hydrophobic derivatives having a substantial amount of groups having the hydrocarbon segments bonded to the polysaccharide backbone (as exemplified by a high DS) are generally more hydrophobic and can be more resistant to degradation. For example, an implant formed from maltodextrin-butyrate DS1 has a rate of degradation that is faster than an implant formed from maltodextrin-butyrate DS2.

The type of hydrocarbon segment present in the groups pendent from the polysaccharide backbone can also influence the hydrophobic properties of the polymer. In one aspect, the implant is formed using a hydrophobic polysaccharide having pendent groups with hydrocarbon segments being short chain branched alkyl group. Exemplary short chain branched alkyl group are branched $C_4$-$C_{10}$ groups. The preparation of a hydrophobic polymer with these types of pendent groups is exemplified by the reaction of maltodextrin with valproic acid/anhydride with maltodextrin (MD-val). The reaction can be carried out to provide a relatively lower degree of substitution of the hydroxyl groups, such as is in the range of 0.5-1.5. Although these polysaccharides have a lower degree of substitution, the short chain branched alkyl group imparts considerable hydrophobic properties to the polysaccharide.

Even at these low degrees of substitution the MD-val forms coatings that are very compliant and durable. Because of the low degrees of substitution, the pendent groups with the branched $C_8$ segment can be hydrolyzed from the polysaccharide backbone at a relatively fast rate, thereby providing a biodegradable coatings that have a relatively fast rate of degradation.

For polysaccharides having hydrolytically cleavable pendent groups that include hydrocarbon segments, penetration by an aqueous solution can promote hydrolysis and loss of groups pendent from the polysaccharide backbone. This can alter the properties of the implant, and can result in greater access to enzymes that promote the degradation of the natural biodegradable polysaccharide.

Various synthetic schemes can be used for the preparation of a hydrophobic derivative of a natural biodegradable polysaccharide. In some modes of preparation, pendent polysaccharide hydroxyl groups are reacted with a compound that includes a hydrocarbon segment and a group that is reactive with the hydroxyl groups. This reaction can provide polysaccharide with pendent groups comprising hydrocarbon segments.

Any suitable chemical group can be coupled to the polysaccharide backbone and provide the polysaccharide with hydrophobic properties, wherein the polysaccharide becomes insoluble in water. Specifically, the pendent group can include one or more atoms selected from carbon (C), hydrogen (H), oxygen (O), nitrogen (N), and sulfur (S).

In some aspects, the pendent group includes a hydrocarbon segment that is a linear, branched, or cyclic $C_2$-$C_{18}$ group. More specifically the hydrocarbon segment includes a $C_2$-$C_{10}$, or a $C_4$-$C_8$, linear, branched, or cyclic group. The hydrocarbon segment can be saturated or unsaturated, and can include alkyl groups or aromatic groups, respectively. The hydrocarbon segment can be linked to the polysaccharide chain via a hydrolyzable bond or a non-hydrolyzable bond.

In some aspects the compound having a hydrocarbon segment that is reacted with the polysaccharide backbone is derived from a natural compound. Natural compounds with hydrocarbon segments include fatty acids, fats, oils, waxes, phospholipids, prostaglandins, thromboxanes, leukotrienes, terpenes, steroids, and lipid soluble vitamins.

Exemplary natural compounds with hydrocarbon segments include fatty acids and derivatives thereof, such as fatty acid anhydrides and fatty acid halides. Exemplary fatty acids and anhydrides include acetic, propionic, butyric, isobutyric, valeric, caproic, caprylic, capric, and lauric acids and anhydrides, respectively. The hydroxyl group of a polysaccharide can be reacted with a fatty acid or anhydride to bond the hydrocarbon segment of the compound to the polysaccharide via an ester group.

The hydroxyl group of a polysaccharide can also cause the ring opening of lactones to provide pendent open-chain hydroxy esters. Exemplary lactones that can be reacted with the polysaccharide include caprolactone and glycolides.

Generally, if compounds having large hydrocarbon segments are used for the synthesis of the hydrophobic derivative, a smaller amount of the compound may be needed for its synthesis. For example, as a general rule, if a compound having a hydrocarbon segments with an alkyl chain length of $C_x$ is used to prepare a hydrophobic derivative with a DS of 1, a compound having a hydrocarbon segment with an alkyl chain length of $C_{(xx}2)$ is reacted in an amount to provide a hydrophobic derivative with a DS of 0.5.

The hydrophobic derivative of the natural biodegradable polysaccharide can also be synthesized having combinations of pendent groups with two or more different hydrocarbon segments, respectively. For example, the hydrophobic derivative can be synthesized using compounds having hydrocarbon segments with different alkyl chain lengths. In one mode of practice, a polysaccharide is reacted with a mixture of two or more fatty acids (or derivatives thereof) selected from the group of acetic acid, propionic acid, butyric acid, isobutyric acid, valeric acid, caproic acid, caprylic acid, capric acid, and lauric acid to generate the hydrophobic derivative.

In other cases the hydrophobic derivative is synthesized having a non-hydrolyzable bond linking the hydrocarbon segment to the polysaccharide backbone. Exemplary non-hydrolyzable bonds include urethane bonds.

The hydrophobic derivative of the natural biodegradable polysaccharide can also be synthesized so that hydrocarbon segments are individually linked to the polysaccharide backbone via both hydrolyzable and non-hydrolyzable bonds. As another example, a hydrophobic derivative is prepared by reacting a mixture of butyric acid anhydride and butyl isocyanate with maltodextrin. This yields a hydrophobic derivative of maltodextrin with pendent butyric acid groups that are individually covalently bonded to the maltodextrin backbone with hydrolyzable ester linkages and non-hydrolyzable urethane linkages. The degradation of a coating having this type of hydrophobic derivative can occur by loss of the butyrate groups from hydrolysis of the ester linkages. However, a portion of the butyrate groups (the ones that are bonded via the urethane groups) are not removed from the polysaccharide backbone and therefore the natural biodegradable polysaccharide can maintain a desired degree of hydrophobicity, prior to enzymatic degradation of the polysaccharide backbone.

In some aspects, the group that is pendent from the polysaccharide backbone has properties of an active pharmaceutical ingredient (API). In this regard, the implants include polysaccharide-coupled API. In some aspects, an API which has a hydrocarbon segment can be hydrolyzed from the natural biodegradable polymer and released from the matrix to provide a therapeutic effect. One example of a therapeutically useful compound having a hydrocarbon segments is butyric acid, which has been shown to elicit tumor cell differentiation and apoptosis, and is thought to be useful for the treatment of cancer and other blood diseases.

Other illustrative compounds that include hydrocarbon segments include valproic acid and retinoic acid. These compounds can be coupled to a polysaccharide backbone to provide a pendent group, and then cleaved from the polysaccharide backbone upon degradation of the implant in vivo. Retinoic acid is known to possess antiproliferative effects and is thought to be useful for treatment of proliferative vitreoretinopathy (PVR). The pendent group that provides a therapeutic effect can also be a natural compound (such as butyric acid, valproic acid, and retinoic acid).

Another illustrative class of compounds that can be coupled to the polysaccharide backbone is the corticosteroids. An exemplary corticosteroid is triamcinolone. One method of coupling triamcinolone to a natural biodegradable polymer is by employing a modification of the method described in Cayanis, E. et al., Generation of an Auto-anti-idiotypic Antibody that Binds to Glucocorticoid Receptor, The Journal of Biol. Chem., 261(11): 5094-5103 (1986). Triamcinolone hexanoic acid is prepared by reaction of triamcinolone with ketohexanoic acid; an acid chloride of the resulting triamcinolone hexanoic acid can be formed and then reacted with the natural biodegradable polymer, such as maltodextrin or polyalditol, resulting in pendent triamcinolone groups coupled via ester bonds to the natural biodegradable polymer.

The hydrophobic derivative of the natural biodegradable polysaccharide can also be synthesized having two or more different pendent groups, wherein at least one of the pendent groups includes an API. The hydrophobic polysaccharide can be synthesized with an amount of a pendent groups including an API, that when released from the polysaccharide, provides a therapeutic effect to the subject. An example of such a hydrophobic derivative is maltodextrin-caproate-triamcinolone. This hydrophobic derivative can be prepared by reacting a mixture including triamcinolone hexanoic acid and an excess of caproic anhydride (n-hexanoic anhydride) with maltodextrin to provide a derivative with a DS of 2.5.

In some aspects, the group that is pendent from the polysaccharide includes a hydrocarbon segment that is an aromatic group, such as a phenyl group. As one example, o-acetylsalicylic acid is reacted with a polysaccharide such as maltodextrin to provide pendent chemical group having a hydrocarbon segment that is a phenyl group, and a non-hydrocarbon segment that is an acetate group wherein the pendent group is linked to the polysaccharide via an ester bond.

Additional features and descriptions of the biodegradable polymers that include the hydrophobic derivatives of natural biodegradable polysaccharides (referred to as Eureka™ SOLO polymers) can be found, for example, in U.S. Patent Publication Nos. 2007/0218102, 2007/0260054 and 2007/0224247, and references cited therein.

A Lipid Composition

The present coating can include or be a lipid composition, which can include a lipid or mixture of lipids. The lipid or mixture of lipids can, for example, be solid (e.g., waxy or paste-like) or semi-solid at room temperature and soft or liquid at the body temperature of a subject.

In an embodiment, the lipid composition includes a lipid with a melting point at or above 40° C. and a lipid with a melting point at or below 20° C. In an embodiment, the lipid composition includes a lipid with a melting point at or above 37° C. and a lipid with a melting point at or below 30° C. In an embodiment, the lipid composition includes a lipid with a melting point of about 35 to about 45° C. and a lipid with a melting point of about 0 to about 35° C.

Lipids that can be employed in the present lipid coating include: a marine oil, such as an oil from herring, menhaden, pilchard, sardine, whale, or a mixture thereof; soybean oil, cottonseed oil, corn oil, peanut oil, sunflower oil, safflower oil, olive oil, palm oil, or a mixture thereof; or mixtures thereof. The lipid composition can be a mixture of a lipid that is liquid at room temperature and a lipid that is solid at room temperature. A lipid that is liquid at room temperature is sold under the trade name High Oleic CV-65 canola oil (Cargill Inc., Minnetonka, Minn.). In an embodiment, the oils that are liquid at room temperature are not hydrogenated (e.g., neither partially hydrogenated nor fully hydrogenated). In an embodiment, the lipid that is solid at room temperature is an oil listed above that is partially or fully hydrogenated, for example, fully hydrogenated. A lipid that is liquid at room temperature is sold under the trade name STABLE FLAKE C® and is a cottonseed stearine product (C. & T. Refinery, Inc. of Richmond, Va.)

In certain embodiments, the lipid composition can include: an oil such as vegetable oil, flower oil, animal oil, marine oil (e.g., fish oil), tropical oil (e.g., coconut oil or palm oil), olive oil, peanut oil; lard, butterfat; a saturated fatty acid, for example, butanoic acid, hexanoic acid, octanoic acid, decanoic acid, dodecanoic acid, tetradecanoic acid, hexadecanoic acid, octadecanoic acid, or a mixture thereof; an unsaturated fatty acid, for example, octadecatrienoic acid, eicosanoic acid, eicosenoic acid, eicosatetraenoic acid, eicosapentaenoic acid, docosahexaenoic acid, palmitoleic acid, stearic acid, oleic acid, vaccenic acid, linoleic acid, alpha-linolenic acid, gamma-linolenic acid, behenic acid, erucic acid, lignoceric acid; a natural or synthetic phospholipids, for example, phosphatidylglycerol, phosphatidic acid, phosphatidylcholine, cardiolipin, phosphatidylethanolamine, phosphatidylserine, phosphatidylinositol, dimyristoylphosphatidylcholine, dioleoylphosphatidylcholine, dipalmitoylphosphatidylcholine, distearoylphosphatidylcholine; a mono-, di-, or triacylglycerol; or mixture thereof. Lard is rendered and clarified pork fat and melts around 86° F. (30° C.).

In certain embodiments, the present lipid composition can include one or more of a fat, a wax, a sterol, a phospholipid; a mono-, di-, or tri-glyceride; a fatty acyl, a glycerolipid, a glycerophospholipid, a sphingolipid (e.g., sphingomyelin), a saccharolipid, a polyketide, a sterol lipid, a prenol lipid, or a mixture thereof. Additional suitable lipids include a ceramide, a phosphosphingolipid, a glycosphingolipid, which can include fatty acid moieties that are saturated or mono-unsaturated with chain lengths from 16 to 26 carbon atoms.

The melting point of the present lipid composition can be determined by any one of a variety of art accepted methods. Suitable methods include the Mettler drop point test (see, e.g., ASTM D 3954). Briefly, in this test the sample to be measured is placed in a cup and heated at a given rate. The temperature at which a drop of molten material passes through a standard orifice is recorded. Other methods include the AOCS Method Cc 2-38 (the Wiley melting point), open capillary slip point, and the softening point tests.

Useful methods for making lipid compositions of that are or appear solid at room temperature and components of these compositions include those described in U.S. Pat. No. 6,544,579, which is incorporated herein by reference. The lipid composition can be cooled at ambient temperature or supercooled to provide the lipid coating.

In an embodiment, the lipid composition consists essentially of one or more lipids. In an embodiment, the lipid composition consists of one or more lipids. The lipid is generally not an active agent.

Fatty Acids

The present lipid composition can include one or more fatty acids, meaning free fatty acid not esterified or otherwise derivatized fatty acid. The fatty acid can include or be a salt of the carboxylic acid (e.g., a salt of the fatty acid). Suitable fatty acids include saturated and unsaturated fatty acids. Suitable unsaturated fatty acids include mono-unsaturated fatty acids and polyunsaturated fatty acids. In an embodiment, the fatty acid composition includes a mono-unsaturated fatty acid. In an embodiment, the fatty acid composition includes a saturated fatty acid. In an embodiment, the fatty acid composition includes a saturated fatty acid and a mono-unsaturated fatty acid.

Suitable saturated fatty acids include those including 6 to 28 carbon atoms. In an embodiment, the saturated fatty acid is of the formula $CH_3(CH_2)_n COOH$, where $4 \leq n \leq 18$. In certain embodiments, n is 4, 5, 6, 7, 8, 9, 10, 11, 12, 13, 14, 15, 16, 17, or 18. In certain embodiments, $6 \leq n \leq 18$, $8 \leq n \leq 16$, or $10 \leq n \leq 14$. In an embodiment, n is 10.

Suitable unsaturated fatty acids include those including 8 to 24 carbon atoms. In an embodiment, the unsaturated fatty acid is of the formula $CH_3(CH_2)_m C=CH(CH_2)_o COOH$, m and o are independently greater than or equal to 2 and less than or equal to 18. In certain embodiments, m is 2, 3, 4, 5, 6, 7, 8, 9, 10, 11, 12, 13, 14, 15, 16, 17, or 18. In certain embodiments, o is 2, 3, 4, 5, 6, 7, 8, 9, 10, 11, 12, 13, 14, 15, 16, 17, or 18. In certain embodiments, $4 \leq m \leq 18$, $6 \leq m \leq 14$, or $6 \leq m \leq 8$. In certain embodiments, $4 \leq o \leq 18$, $6 \leq o \leq 14$, or $6 \leq o \leq 8$. In an embodiment, m is 7, o is 11 and the double bond is cis. In an embodiment, the unsaturated fatty acid is of the formula $CH_2=CH(CH_2)_p COOH$ with $3 \leq p \leq 21$.

In an embodiment, the unsaturated fatty acid can be described by C:D where C is the number of carbon atoms and D is the number of double bonds. C can be 6 to 24 and D can be 2 to 6. C and D are integers. In an embodiment, D can be 1 and C can be 6 to 24. The locations and stereochemistry of the double bond can be specified also.

In an embodiment, the fatty acid composition includes a saturated fatty acid with a melting point at or above 30° C. and an unsaturated fatty acid with a melting point at or below 20° C. In an embodiment, the fatty acid composition includes a saturated fatty acid with a melting point at or above 35° C. and an unsaturated fatty acid with a melting point at or below 35°

C. In an embodiment, the fatty acid composition includes a saturated fatty acid with a melting point of about 30 to about 45° C. and an unsaturated fatty acid with a melting point of about 0 to about 35° C.

In an embodiment, the lipid coating includes or is made of a plurality of fatty acids. The plurality of fatty acids can be two fatty acids. The lipid coating can be a fatty acid or mixture of (e.g. two) fatty acids. The fatty acid or fatty acids can be a composition that is or that makes up the barrier layer. The plurality of fatty acids can be a mixture of fatty acids that are solid at room temperature and soft or liquid at body temperature of the subject. The plurality of fatty acids can be a mixture of fatty acids having a softening temperature greater than room temperature and less than body temperature of the subject. The plurality of fatty acids can be a mixture of fatty acids having a melting point greater than room temperature and less than body temperature of the subject.

Phospholipids

In an embodiment, the lipid composition includes a phospholipid. Suitable phospholipids include, for example, a phosphatidic acid, a phosphatidylcholine, a phosphatidylethanolamine, a phosphatidylserine, or mixture thereof.

Suitable phosphatidylcholines include, for example: 1,2-Didecanoyl-sn-glycero-3-phosphocholine (CAS no. 3436-44-0), 1,2-Dierucoyl-sn-glycero-3-phosphocholine (CAS no. 56649-39-9), 1,2-Dilinoleoyl-sn-glycero-3-phosphocholine (CAS no. 998-06-1), 1,2-Dilauroyl-sn-glycero-3-phosphocholine (CAS no. 18194-25-7), 1,2-Dimyristoyl-sn-glycero-3-phosphocholine (CAS no. 18194-24-6), 1,2-Dioleoyl-sn-glycero-3-phosphocholine (CAS no. 4235-95-4), 1,2-Dipalmitoyl-sn-glycero-3-phosphocholine (CAS no. 63-89-8), phosphatidylcholine purified from egg, phosphatidylcholine purified from soybean, lysophosphatidylcholine, 1-Myristoyl-2-palmitoyl-sn-glycero 3-phosphocholine, 1-Myristoyl-2-stearoyl-sn-glycero-3-phosphocholine, 1-Palmitoyl-2-myristoyl-sn-glycero-3-phosphocholine, 1-Palmitoyl-2-oleoyl-sn-glycero-3-phosphocholine (CAS no. 26853-31-6), 1,2-Distearoyl-sn-glycero-3-phosphocholine (CAS no. 816-94-4), 1-Palmitoyl-2-stearoyl-sn-glycero-3-phosphocholine, 1-Stearoyl-2-myristoyl-sn-glycero-3-phosphocholine, 1-Stearoyl-2-oleoyl-sn-glycero-3-phosphocholine, 1-Stearoyl-2-palmitoyl-sn-glycero-3-phosphocholine, or mixture thereof.

Suitable lysophosphatidylcholines include, for example: 1-Myristoyl-sn-glycero-3-phosphocholine (CAS no. 18194-24-6), 1-Palmitoyl-sn-glycero-3-phosphocholine (CAS no. 17364-16-8), 1-Stearoyl-sn-glycero-3-phosphocholine (CAS no. 19420-57-6), or mixture thereof.

Suitable phosphatidic acids include, for example: 1,2-Dierucoyl-sn-glycero-3-phosphate (Sodium Salt) (CAS no. 80724-31-8), 1,2-Dilauroyl-sn-glycero-3-phosphate (Sodium Salt), 1,2-Dimyristoyl-sn-glycero-3-phosphate (Sodium Salt) (CAS no. 80724-3), 1,2-Dioleoyl-sn-glycero-3-phosphate (Sodium Salt), 1,2-Dipalmitoyl-sn-glycero-3-phosphate (Sodium Salt) (CAS no. 71065-87-7), 1,2-Distearoyl-sn-glycero-3-phosphate (Sodium Salt) (CAS no. 108321-18-2), or mixture thereof.

Suitable phosphatidylethanolamines include, for example: 1,2-Dierucoyl-sn-glycero-3-phosphoethanolamine (CAS no. 988-07-2), 1,2-Dilauroyl-sn-glycero-3-phosphoethanolamine, 1,2-Dimyristoyl-sn-glycero-3-phosphoethanolamine (CAS no. 988-07-2), 1,2-Dioleoyl-sn-glycero-3-phosphoethanolamine, 1,2-Dipalmitoyl-sn-glycero-3-phosphoethanolamine (CAS no. 923-61-5), 1-Palmitoyl-2-oleoyl-sn-glycero-3-phosphoethanolamine, 1,2-Distearoyl-sn-glycero-3-phosphoethanolamine (CAS no. 1069-79-0), or mixture thereof.

Suitable phosphatidylserines include, for example: 1,2-Dilauroyl-sn-glycero-3-phosphoserine (Sodium Salt), 1,2-Dimyristoyl-sn-glycero-3-phosphoserine (Sodium Salt), 1,2-Dipalmitoyl-sn-glycero-3-phosphoserine (Sodium Salt), 1,2-Distearoyl-sn-glycero-3-phosphoserine (Sodium Salt), 1,2-Dioleoyl-sn-glycero-3-phosphoserine (Sodium Salt) (CAS no. 70614-14-1), or mixture thereof.

Applying the Coating

Referring now to FIGS. 1 and 2, a method for applying an embodiment of the coating 90 to the catheter assembly 10 will now be described. The coating 90 is heated so that the coating 90 is in a flowable state. Doses of the coating 90 are then measured using a pipette. In one embodiment, the doses are in a range of about 5 to 10 µL.

Fluid is communicated to the lumen 30 of the expandable and collapsible structure 12 so that the catheter assembly 10 is in an unfolded state. In one embodiment, the lumen 30 is pressurized to about 1 to 2 atmospheres. With the expandable and collapsible structure 12 in an unfolded state, the reservoirs 46 are accessible.

A nozzle of the pipette is positioned at the opening 48 of the reservoir 46. The dose of coating 90 is injected into each of the reservoirs 46. The catheter assembly 10 is then cooled so that the coating 90 returns to a non-flowable state.

In another embodiment, fluid is communicated to the lumen 30 of the expandable and collapsible structure 12 so that the expandable and collapsible structure 12 is in an unfolded state. In one embodiment, the fluid communicated to the lumen 30 has a pressure of 1 to 2 atmospheres. With the expandable and collapsible structure 12 in an unfolded state, the reservoirs 46 are accessible.

The coating 90 is applied to the outer surface 22 of the expandable and collapsible structure 12 and the exterior surface 38 of the guard 14. The coating 90 can be applied using a pipette or a plurality of pipettes. Alternatively, the coating 90 can be spread over the exterior surface 38 of the guard 14.

A sheath is then placed around the exterior surface 38 of the guard 14. The sheath is a tight-fitting sheath. With the sheath disposed over the catheter assembly 10, the catheter assembly 10 is heated. In one embodiment, the catheter assembly 10 is heated by controlling the temperature of the fluid that enters the lumen 30. As the catheter assembly 10 is heated, the coating 90 becomes flowable so that the coating is uniformly distributed in the reservoirs 46 of the catheter assembly 10.

With the coating 90 disposed in the reservoirs 46, the catheter assembly 10 is allowed to cool so that the coating 90 returns to its non-flowable state. Once the catheter assembly 10 has cooled, the sheath is removed. As the sheath is removed, most of the coating 90 disposed on the exterior surface 38 of the guard 14 is removed while the coating 90 in the reservoirs 46 remains.

Figure 9:
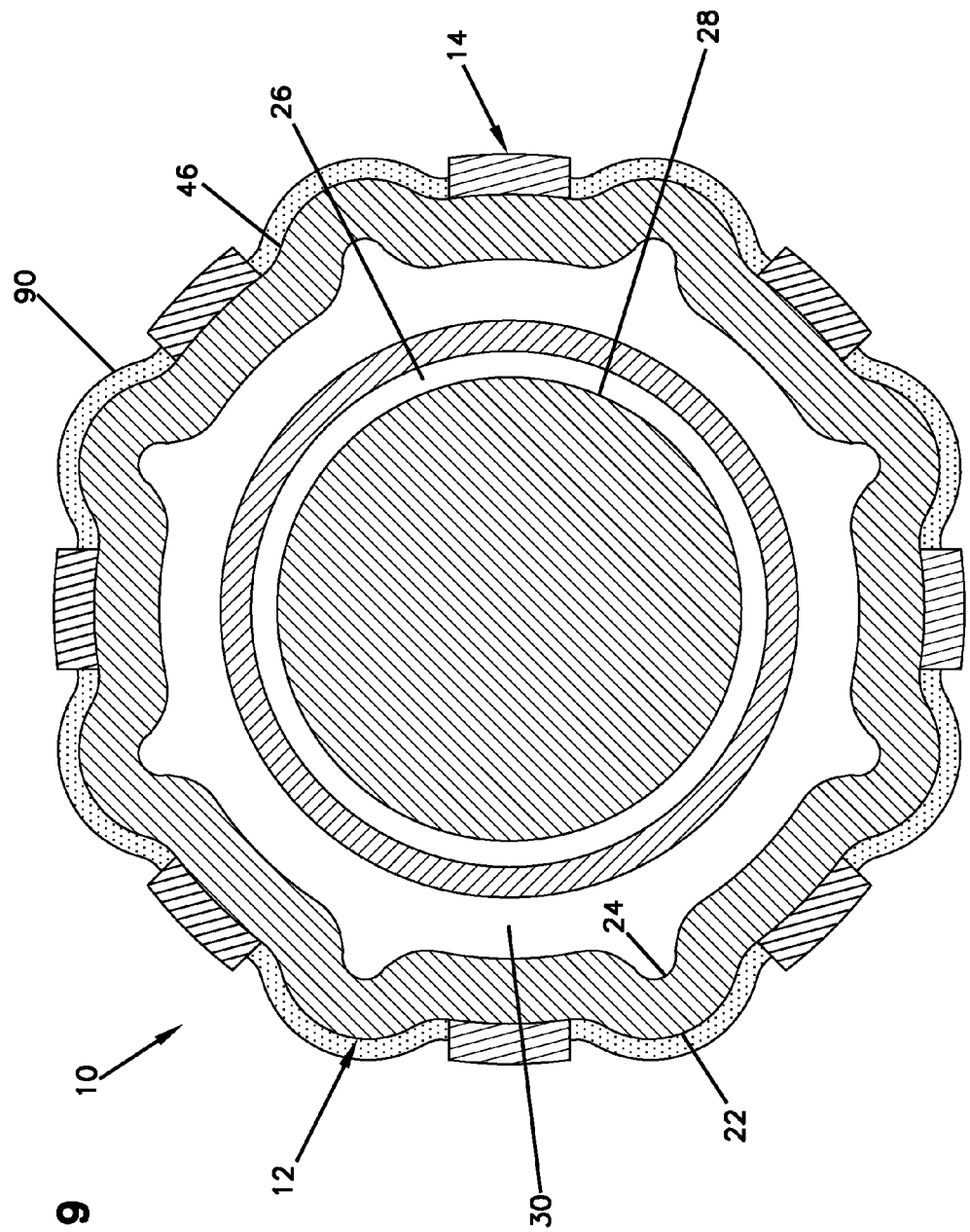
FIG. 9 is a cross-sectional view of the catheter assembly of FIG. 1 in a dilated state.

Referring now to FIGS. 1, 2 and 9, the use of the catheter assembly 10 will be described. When the catheter assembly 10 is positioned at the target site in the body of the patient, fluid is communicated to the lumen 30 of the expandable and collapsible structure 12 so that the expandable and collapsible structure 12 expands to the dilated state (shown in FIG. 8). The pressure of the fluid creates a force that acts against the inner surface 24 of the expandable and collapsible structure 12 causing dilation of the expandable and collapsible structure 12. In one embodiment, the fluid pressure required to expand the expandable and collapsible structure 12 to the dilated state is less than or equal to about 10 atmospheres of pressure. In another embodiment, the fluid pressure required to expand the expandable and collapsible structure 12 to the dilated state is in a range of about 4 to 10 atmospheres of pressure.

While the expandable and collapsible structure 12 is flexible, the guard 14 is less flexible. Therefore, as fluid is provided to the lumen 30 of the expandable and collapsible structure 12, the expandable and collapsible structure 12 expands through the orifices 44 in the guard 14. As the guard 14 is affixed to the expandable and collapsible structure 12, the expansion of the expandable and collapsible structure 12 pushes the contents of the reservoirs 46 outwardly beyond the outer diameter of the exterior surface 38 of the guard 14. As the contents of the reservoirs 46 are pushed outward from the catheter assembly 10, the contents are transferred to the target site delivering known doses of medication to the target site.

As the guard 14 is affixed to the expandable and collapsible structure 12, the guard 14 is prevented moving relative to the expandable and collapsible structure 12 at the interface between the expandable and collapsible structure 12 and the guard 14. This prevents the guard 14 from scraping the coating 90 disposed in the reservoirs 46 off the outer surface 22 of the expandable and collapsible structure 12.

Various modifications and alterations of this disclosure will become apparent to those skilled in the art without departing from the scope and spirit of this disclosure, and it should be understood that the scope of this disclosure is not to be unduly limited to the illustrative embodiments set forth herein.

What is claimed is:

1. A catheter assembly comprising:
   an expandable and collapsible structure having an outer surface and an interior surface, wherein a lumen is disposed between the interior surface and a guide passage, the expandable and collapsible structure being adapted to expand between a contracted state and a dilated state;
   a guard bonded to the outer surface of the expandable and collapsible structure, wherein the guard includes an interior surface bonded to the outer surface of the expandable and collapsible structure and an exterior surface opposite the interior surface;
   wherein the guard defines a plurality of orifices that extend through the interior and exterior surfaces cooperatively defining a plurality of reservoirs;
   and a coating disposed in the reservoirs, the coating including a bioactive agent, wherein the coating protrudes from the reservoirs when the expandable and collapsible structure is expanded to the dilated state.

2. The catheter assembly of claim 1, wherein the guard is thermally bonded to the outer surface of the expandable and collapsible structure.

3. The catheter assembly of claim 1, wherein the guard is bonded to the outer surface of the expandable and collapsible structure by an adhesive.

4. The catheter assembly of claim 1, wherein the expandable and collapsible structure is made of a first material and the guard is made of a second material.

5. The catheter assembly of claim 4, wherein the second material is less flexible than the first material.

6. The catheter assembly of claim 4, wherein the second material is different from the first material.

7. The catheter assembly of claim 1, wherein the orifices are generally chevron shaped.

8. The catheter assembly of claim 1, wherein the orifices are channels that extend circumferentially around the expandable and collapsible structure.

9. The catheter assembly of claim 1, wherein the guard includes a fold line that extends between a first axial end of the guard and an oppositely disposed second axial end.

10. The catheter assembly of claim 9, wherein the fold line has a reduced thickness.

11. The catheter assembly of claim 1, wherein the coating includes an agent coating having a bioactive agent and a protective coating having a fatty acid, the protective coating being disposed on the agent coating.

12. The catheter assembly of claim 11, wherein the protective coating includes a plurality of fatty acids.

13. The catheter assembly of claim 12, wherein the plurality of fatty acids is solid at room temperature and soft or liquid at a body temperature of a subject.

14. A catheter assembly comprising:
   an expandable and collapsible structure having an outer surface and an interior surface, wherein a lumen is disposed between the interior surface and a guide passage, the expandable and collapsible structure being adapted to expand between a contracted state and a dilated state, the expandable and collapsible structure being made of a first material;
   a guard bonded to the outer surface of the expandable and collapsible structure, the guard being made of a second material that is less flexible than the first material, the guard and the expandable and collapsible structure cooperatively defining a plurality of reservoirs with the outer surface of the expandable and collapsible structure forming base walls of the reservoirs and the guard forming sidewalls of the reservoirs;
   and a coating disposed in the reservoirs, the coating including a bioactive agent, wherein the coating protrudes from the reservoirs when the expandable and collapsible structure is expanded to the dilated state.

15. The catheter assembly of claim 14, wherein an interior surface of the guard is bonded to the outer surface of the expandable and collapsible structure.

16. The catheter assembly of claim 14, wherein the guard is thermally bonded to the outer surface of the expandable and collapsible structure.

17. The catheter assembly of claim 14, wherein the guard is bonded to the outer surface of the expandable and collapsible structure by an adhesive.

18. The catheter assembly of claim 14, wherein the second material is different from the first material.

19. The catheter assembly of claim 14, wherein the second material is thicker than the first material.

20. The catheter assembly of claim 14, wherein the guard includes: an interior surface bonded to the outer surface of the expandable and collapsible structure; an exterior surface opposite the interior surface; wherein the guard defines a plurality of orifices that extend through the interior and exterior surfaces.

21. The catheter assembly of claim 20, wherein the orifices are generally chevron shaped.

22. The catheter assembly of claim 20, wherein the orifices are channels that extend circumferentially around the expandable and collapsible structure.

23. The catheter assembly of claim 14, wherein the guard includes a fold line that extends between a first axial end of the guard and an oppositely disposed second axial end.

24. The catheter assembly of claim 23, wherein the fold line has a reduced thickness.

25. The catheter assembly of claim 14, wherein the coating includes an agent coating having a bioactive agent and a protective coating having a fatty acid, the protective coating being disposed on the agent coating.

26. The catheter assembly of claim 25, wherein the protective coating includes a plurality of fatty acids.

27. The catheter assembly of claim 26, wherein the plurality of fatty acids is solid at room temperature and soft or liquid at a body temperature of a subject.

28. A catheter assembly comprising:
an expandable and collapsible structure having an outer surface and an interior surface, wherein a lumen is disposed between the interior surface and a guide passage, the expandable and collapsible structure being adapted to expand between a contracted state and a dilated state;
a guard disposed on the outer surface of the expandable and collapsible structure, the guard including a fold line that extends between a first end of the guard and an oppositely disposed second end, the fold line having an area of reduced thickness, the guard and the expandable and collapsible structure cooperatively defining a plurality of reservoirs with the outer surface of the expandable and collapsible structure forming base walls of the reservoirs and the guard forming sidewalls of the reservoirs;
and a coating disposed in the reservoirs, the coating including a bioactive agent, wherein the coating protrudes from the reservoirs when the expandable and collapsible structure is expanded to the dilated state.

29. A method of applying a coating to a catheter assembly, the method comprising: heating a coating so that the coating is in a flowable state;
applying a measured amount of the coating to reservoirs cooperatively defined by an expandable and collapsible structure and a guard,
wherein the expandable and collapsible structure has an outer surface, an interior surface., and a lumen disposed between the interior surface and a guide passage, and wherein the guard includes an interior surface bonded to the outer surface of the expandable and collapsible structure and an exterior surface opposite the interior surface;
wherein the guard defines a plurality of orifices that extend through the interior and exterior surfaces;
and cooling the coating so that the coating is in a non-flowable state.

30. The method of claim 29, wherein the coating is applied to the reservoirs through a pipette.

31. The method of claim 29, wherein the measured amount is in the range of about 5 µL, to about 10 µL.

32. The method of claim 29, wherein the coating includes an agent coating having a bioactive agent and a protective coating having a fatty acid, the protective coating being disposed on the agent coating.

33. The catheter assembly of claim 32, wherein the protective coating includes a plurality of fatty acids.

34. The catheter assembly of claim 33, wherein the plurality of fatty acids is solid at room temperature and soft or liquid at a body temperature of a subject.

35. A method of applying a coating to a catheter assembly, the method comprising:
applying a coating to an exterior surface of a guard that is affixed to an expandable and collapsible structure of a catheter assembly, wherein the expandable and collapsible structure has an outer surface, an interior surface, and a lumen disposed between the interior surface and a guide passage, and wherein the guard and the expandable and collapsible structure define a plurality of reservoirs having openings at the exterior surface of the guard;
placing the guard and expandable and collapsible structure in an inner bore of a sheath; heating the coating so that the coating is in a flowable state;
and sliding the guard and expandable and collapsible structure out of the sheath so that coating on the exterior surface of the guard is substantially removed.

36. The method of claim 35, wherein the coating includes an agent coating having a bioactive agent and a protective coating having a fatty acid, the protective coating being disposed on the agent coating.

37. The method of claim 36, wherein the protective coating includes a plurality of fatty acids.

38. The method of claim 37, wherein the plurality of fatty acids is solid at room temperature and soft or liquid at a body temperature of a subject.

* * * * *